(12) United States Patent
Gei et al.

(10) Patent No.: US 11,872,395 B2
(45) Date of Patent: Jan. 16, 2024

(54) PESSARY DEVICE AND METHODS FOR PREVENTING PREMATURE BIRTHS

(71) Applicant: OBSTETRIC SOLUTIONS LLC, Houston, TX (US)

(72) Inventors: Alfredo F. Gei, Houston, TX (US); David Esteban Paniagua Gonzalez, Houston, TX (US); David Paniagua, Houston, TX (US)

(73) Assignee: Obstetric Solutions, LLC, Houston, TX (US)

( * ) Notice: Subject to any disclaimer, the term of this patent is extended or adjusted under 35 U.S.C. 154(b) by 1143 days.

(21) Appl. No.: 16/444,279

(22) Filed: Jun. 18, 2019

(65) Prior Publication Data
US 2020/0398052 A1    Dec. 24, 2020

(51) Int. Cl.
*A61N 1/36*    (2006.01)
*A61B 5/145*    (2006.01)
(Continued)

(52) U.S. Cl.
CPC ............ *A61N 1/36007* (2013.01); *A61B 5/01* (2013.01); *A61B 5/1126* (2013.01);
(Continued)

(58) Field of Classification Search
CPC ......... A61F 6/08; A61N 1/0524; A61B 5/435; A61B 5/4356; A61M 2210/1475
See application file for complete search history.

(56) References Cited

U.S. PATENT DOCUMENTS

| | | | | |
|---|---|---|---|---|
| 436,861 A | * | 9/1890 | Sherwood | A61F 6/08 128/835 |
| 2,020,107 A | * | 11/1935 | Cruickshank | A61F 6/08 128/832 |

(Continued)

FOREIGN PATENT DOCUMENTS

| | | |
|---|---|---|
| WO | 2016199115 A2 | 12/2016 |
| WO | 2017152029 A1 | 9/2017 |

(Continued)

OTHER PUBLICATIONS

"Association between preterm labour and pelvic floor muscle function". Aran, T et al. Journal of Obstetrics and Gynaecology. vol. 38, Issue 8. 2018.*

(Continued)

*Primary Examiner* — Brandy S Lee
*Assistant Examiner* — John J Crawford
(74) *Attorney, Agent, or Firm* — Marc Delflache; Jones Delflache LLP

(57) ABSTRACT

A pessary for the prevention of preterm birth, and in particular two pathological conditions of pregnancy known as isthmico-cervical incontinence and cervical shortening, both of which are associated with increased risks for pregnancy loss and/or premature deliveries of babies. The pessary includes a sleeve supported within a ring by an annular member. The sleeve is intended to contact the cervix and maximize the length of the cervix while the annular member and ring contact the vagina. The pessary may be fabricated from a pliable medical-grade silicon, and the pessary may include one or more sensors to measure various patient parameters indicative of a premature cervical contraction.

40 Claims, 13 Drawing Sheets

(51) Int. Cl.
| | |
|---|---|
| *A61B 5/01* | (2006.01) |
| *A61B 5/11* | (2006.01) |
| *A61B 5/00* | (2006.01) |
| *A61M 31/00* | (2006.01) |
| *A61F 6/08* | (2006.01) |
| *A61K 31/57* | (2006.01) |

(52) U.S. Cl.
CPC .......... *A61B 5/14539* (2013.01); *A61B 5/435* (2013.01); *A61B 5/4356* (2013.01); *A61B 5/6847* (2013.01); *A61F 6/08* (2013.01); *A61K 31/57* (2013.01); *A61M 31/00* (2013.01); *A61M 2205/3324* (2013.01); *A61M 2210/1475* (2013.01); *A61M 2230/50* (2013.01); *A61M 2230/63* (2013.01)

(56) References Cited

U.S. PATENT DOCUMENTS

| | | | | |
|---|---|---|---|---|
| 2,818,064 | A * | 12/1957 | Leff | A61F 6/08 128/841 |
| 3,404,682 | A * | 10/1968 | Waldron | A61F 13/26 128/838 |
| 4,311,543 | A | 1/1982 | Strickman et al. | |
| 4,517,970 | A * | 5/1985 | Goepp | A61F 6/08 128/841 |
| 4,711,235 | A | 12/1987 | Willis | |
| 5,065,772 | A | 11/1991 | Cox | |
| 5,207,232 | A * | 5/1993 | Shihata | A61F 6/08 128/838 |
| 6,086,909 | A * | 7/2000 | Harrison | A61K 9/0036 424/431 |
| 8,408,212 | B2 | 4/2013 | O'Brien et al. | |
| 8,573,221 | B2 | 11/2013 | Sakhel | |
| 9,474,885 | B2 | 10/2016 | Cline et al. | |
| 9,764,120 | B2 | 9/2017 | Cline et al. | |
| 9,820,994 | B2 | 11/2017 | Campos Perez et al. | |
| 2006/0260619 | A1* | 11/2006 | Moench | A61F 6/08 128/837 |
| 2013/0053670 | A1 | 2/2013 | Aina-Mumuney et al. | |
| 2014/0073879 | A1* | 3/2014 | Cantor | A61B 5/435 600/304 |
| 2015/0265456 | A1* | 9/2015 | Booher, Sr. | A61F 6/08 128/836 |
| 2017/0020529 | A1* | 1/2017 | Tsur | A61M 31/00 |
| 2019/0008674 | A1* | 1/2019 | Myers | A61F 6/08 |
| 2019/0160332 | A1* | 5/2019 | Beer | A61B 5/227 |
| 2020/0086110 | A1* | 3/2020 | Karsdon | A61N 1/0524 |

FOREIGN PATENT DOCUMENTS

| | | | | | |
|---|---|---|---|---|---|
| WO | WO-2017152029 | A1 * | 9/2017 | | A61F 6/08 |
| WO | 2018119052 | A1 | 6/2018 | | |
| WO | WO-2019226441 | A1 * | 11/2019 | | A61B 17/42 |
| WO | WO-2020140075 | A1 * | 7/2020 | | A61F 6/08 |

OTHER PUBLICATIONS

Alfirevic, Z., et al., "Vaginal progesterone, cerclage or cervical pessary for preventing preterm birth in asymptomatic singleton pregnant women with a history of preterm birth and a sonographic short cervix," Ultrasound Obstet. Gynecol, Feb. 2013 (6 pages).
Berghella, V., et al., "Prevention of preterm birth with pessary in twins (PoPPT): a randomized controlled trial," Ultrasound Obstet Gynecol. May 2017 (2 pages).
Berghella, V., et al., "Twins with short cervix: hope ahead," BJOG: An International Journal of Obstetrics and Gynaecology, (1 page).
Biggio, J. et al., "Spontaneous Preterm Birth in Multiples," Clinical Obstetrics and Gynecology, vol. 58, No. 3, pp. 654-657 (14 pages).
Cabrera-Garcia, L., et al., "Evaluation of two treatment strategies fore the prevention of preterm birth in women identified as a risk by ultrasound (PESAPRO Trial): study protocol for a randomized controlled trial," Trials: Study Protocol (10 pages).
Cannie, M., et al., "Arabin cervical pessary in women at high risk of preterm birth: a magnetic resonance imaging observational follow-up study," Ultrasound Obstet. Gynecol 2013 (8 pages).
Collins, A., et al., "A clinical opinion on how to manage the risk of preterm birth in twins based on literature review," The Journal of Maternal-Fetal & Neonatal Medicine, May 22, 2015. (7 pages).
Dharan, V., et al., "Alternative Treatment for a Short Cervix: The Cervical Pessary," Elsevier: Seminars in Perinatology, 2009 (5 pages).
Ditommaso, M., et al., "Arabin cervical pessary to prevent preterm birth in twin pregnancies with short cervix," Journal of Obstetrics and Gynaecology, 2016 (5 pages).
Dugoff, I., et al., Prevention of preterm birth with pessary in singletons (PoPPS): randomized controlled trial Ultrasound Obstet. Gynecol, 2018 (8 pages).
Folterman, C., "Cervical Pessary and Vaginal Progesterone in Twin Pregnancies with a Short Cervix," The American College of Obstetricians and Gynecologists, Aug. 2016 (2 pages).
Fox, N., et al., "Cervical Pessary and Vaginal Progesterone in Twin Pregnancies with a Short Cervix," Obstetrics & Gynecology, vol. 127, No. 4, Apr. 2016 (6 pages).
Fuchs, F., et al., "Multiple gestations and preterm birth," Seminars in Fetal & Neonatal Medicine, 2016 (8 pages).
Gilner, J., et al., "Management of Short Cervix during Pregnancy", American Journal of Perinatology, Review Prematurity Special Issue, vol. 33, No. 3, 2016 (8 pages).
Goya, M. et al., Cervical pessary in pregnant women with a short cervix (PECEP): an open-label randomised controlled trial, www.thelancet.com, vol. 379, May 12, 2012 (3 pages).
Goya, M. et al., Cervical pessary to prevent preterm birth in women with twin gestation and sonographic short cervix: a multicenter randomized controlled trial (PECEP-Twins), American Journal of Obstetrics & Gynecology, Feb. 2016 (8 pages).
H., A., et al., Cervical pessary for preventing preterm birth (Review), The Cochrane Collaboration, 2013, Issue 5, Art. No. CD007873 (29 pages).
Hermans, F., et al., Effectiveness of a cervical pesary for women who did not deliver 48 h after threatened preterm labor (Assessment of perinatal outcome after specific treatment in early labor: Apostel VI trial), BMC Pregnancy and Childbirth, 2016 (6 pages).
Hezelgrave, N., et al., "Rationale and design of SuppOrt: a multi-centre randomised controlled trial to compare three treatments: cervical cerclage, cervical pessary and vaginal progesterone, for the prevention of preterm birth in women who develop a short cervix," BMG Pregnancy and Childbirth: 2016 (10 pages).
Houda, M., et al., "Cervical pessary in in pregnant women with a short cervix," www.thelancet.com, vol. 380, Sep. 8, 2012 (2 pages).
Hui, A., et al., "Cerclage Pessary for Preventing Preterm Birth in Women with a Singleton Pregnancy and a Short Cervix at 20 to 24 Weeks: A Randomized Controlled Trial," American Journal of Perinatology, vol. 30, No. 4, 2013 (6 pages).
Huras, H., et al., "Short cervix in twin pregnancies: current state of knowledge and the proposed scheme of treatment," Ginekologia Polska 2017, vol. 88, No. 11 (7 pages).
Jarde, A., et al, "Effectiveness of progesterone, cerclage and pessary for preventing preterm birth in singleton pregnancies: a systematic review and network meta-analysis," BJOG: An International Journal of Obstetrics and Gynaecology, 2017 (14 pages).
Jin, X., et al., "Cervical Pessary for Prevention of Preterm Birth: a Meta-Analysis," www.nature.com/scientificreports.com, 2017 (6 pages).
Kalinka, J., et al., "Rupture of the cervix during pregnancy after cervical pessary insertion for preventing preterm birth," The Journal of Obstetrics and Gynaecology Research, vol. 42, No. 12, 2016 (4 pages).
Karisallen, L., et al., "Retrospective Cohort Study of Cervical Pessary Use in Women with Short Cervix at Risk of Preterm Delivery," J. Obstet. Gynaecol Can., 2017 (6 pages).
Khalifeh, A., et al., "Not transabdominal!", American Journal of Obstetrics & Gynecology, Dec. 2016 (7 pages).

(56) References Cited

OTHER PUBLICATIONS

Klein, K., et al., "Vaginal micronized progesterone and risk of preterm delivery in high-risk twin pregnancies: secondary analysis of a placebo-controlled randomized trial and meta-analysis," Ultrasound Obstet. Gynecol, 2011 (7 pages).
Koullali, B., et al., "A multi-centre, non-inferiority, randomised controlled trial to compare a cervical pessary with a cervical cerclage in the prevention of preterm delivery in women with short cervical length and a history of preterm birth—PC Study," BMC Pregnancy and Childbirth, 2017 (9 pages).
Liem, S., et al., "Cervical pessaries to prevent preterm birth in women with a multiple pregnancy: a per-protocol analysisof a randomized clinical trial," AOGS, 2016 (8 pages).
Makrydimas, G., "Vaginal progesterone, cerclage or cervical pessary for preventing preterm birth in asymptomatic singleton pregnant women with history of preterm birth and a sonographic short cervix," Ultrasound Obstet. Gunecol, 2013 (1 page).
Marasinghe, J., "Cervical Pessary and Vaginal Progesterone in Twin Pregnannies with a Short Cervix:", Obstet. Gynacol, Aug. 2016 (1 page).
Melendez, J., et al., "Cervical pessary in pregnant women with a short cervix," Lancet. Sep. 2012 (2 pages).
Mendoza, M., et al., "Modification of cervical length after cervical pessary insertion: correlation weeks of gestation," The Journal of Maternal-Fetal & Neonatal Medicine, Aug. 28, 2016 (7 pages).
Merced, C., et al., "Cervical pessary for preventing preterm birth in twin pregnancies with maternal short cervix after an episode of threatened preterm labor: randomised controlled trial," Am. J. Obstet. Gynecol., Feb. 28, 2019 (14 pages).
Nicolaides, K., et al., "A Randomized Trial of a Cervical Pessary to Prevent Preterm Singleton Birth," The New England Journal of Medicine, Mar. 17, 2016 (9 pages).
Nicolaides, K., et al., "Cervical pessary placement for prevention of preterm birth in unselected twin pregnancies: a randomized controlled trial," Am. J. Obstet. Gynecol., Jan. 2016 (9 pages).
Pratcorona, L., et al., "Cervical pessary to reduce preterm birth less than 34 weeks of gestation after an episode of preterm labor and a short cervix: a randomized controlled trial," Amer. J. Obstet. Gynecol., Jul. 2018 (16 pages).
Saccone, G., et al., "Cervical Pessary for Preventing Preterm Birth in Singleton Pregnancies with Short Cervical Length," J. Ultrasound Med. Aug. 2017, (9 pages).
Saccone, G., et al., "Cervical Pessary for Preventing Preterm Birth in Twin Pregnancies with Short Cervical Length: a systematic review and meta-analysis" J. Matern. Fetal Neonatal Med. Dec. 2017 (9 pages).
Saccone, G., et al., "Effect of Cervical Pessary on Spontaneous Preterm Birth in Women with Singleton Pregnancies and Short Cervical Length—A Randomized Clinical Trial," JAMA, Dec. 2017 (8 pages).
Saccone, G., et al., Effects of Exercise During Pregnancy in Women with Short Cervis: Secondary analysis from the Italian Pessary Trial in Singletons, Eur. J. Obstet. Gynecol. Reprod. Biol. Oct. 2018, (6 pages).
Sharp, A., et al., "Provision and practice of specialist preterm labour clinics: a UK survey of practice," BJOG.org, Mar. 2014 (5 pages).
Stricker, N., et al., "Vaginal progesterone combined with cervical pessary: A chance for pregnancies at risk for preterm birth?", Am. J. Obstet. Gynecol. Jun. 2016 (11 pages).
Tajik, P., et al., A multivariable model to guide the decision for pessary placement to prevent preterm birth in women with a multiple pregnancy: a secondary analysis of the ProTWIN trial, Ultrasound Obstet. Gynecol, Jul. 2016 (8 pages).
Thangatorai, R., et al., "Cervical pessary in the prevention of preterm births in multiple pregnancies with a short cervix: PRISMA compliant systematic review and meta-analysis," J. Matern. Fetal Neonatal Med. Jun. 2018 (14 pages).
Van 'T Hooft, J., et al., "Pessary for prevention of preterm birth in twin pregnancy with short cervix: 3-year follow-up study," Ultrasound Obstet. Gynecol. May 2018 (8 pages).

Van Zijl, M. et al., "Pessary or Progesterone to Prevent Preterm delivery in women with short cervical length: the Quadruple P randomized controlled trial," BMC Pregnancy Childbirth Sep. 2017 (8 pages).
Van Zijl, M. et al., "Prevention of preterm delivery: current challenges and future prospects," Int. J. Womens Health, Oct. 2016, (13 pages).
Vintzileos, A.M., et al., "Interventions for women with mid-trimester short cervix: which ones work?", BJOG, Jul. 2017 (6 pages).
Cross, R., "Treatment of habitual abortion due to cervical incompetence", Lancet 1959:2:127.
Kindinger, L., et al., "The interaction between vaginal microbiota, cervical length, and vaginal progesterone treatment for preterm birth risk," Microbiome (2017) (14 pages).
Iams, J.D., et al., "The length of the cervix and the risk of spontaneous premature delivery", N. Engl. J. Med. 1996:334:567-572.
Berghella, V., "Universal Cervical Length Screening for Prediction and Prevention of Preterm Birth," Obstetrical and Gynecological Survey, vol. 67, No. 10 (2012).
Liem, S.M.S, et al., "Cervical Pessaries for the Prevention of Preterm Birth: A Systematic Review". Obstetrics and Gynecology International 2013: 1-10.
McDonald, I.A., "Suture of the cervix for inevitable miscarriage", J. Obstet. Gynaecol. Br. Emp 1957:64:712-714.
Boiko, V., et al., "The problem of miscarriage in multiple pregnancy," 2018, Sumy State University, Sumy, Ukraine, 13 pages.
Oster, S., et al., "Treatment of the incompetent cervix with the Hodge pessary", Obstet. Gynecol. 1966:28:206-208.
Shirodkar, V.N., "A new method of operative treatment for habitual abortion in the second trimester of pregnancy", Antiseptic 1955:52:299.
Vitsky, M., "Simple treatment of the incompetent cervical os", Am.J.Obst. & Gynec. Jun. 1961, vol. 81, No. 6, 1194-1197 (4 pages).
Daskalakis, G., et al., "Safety and efficacy of the cervical pessary combined with vaginal progesterone for the prevention of spontaneous preterm birth," Journal of Perinatal Medicine, Jul. 26, 2018 (8 pages).
Louras, G.M., et al., "Successful pregnancy with the use of vaginal pessary in a patient with a very short cervix," Societa Editrice Universo, Clin. Ter. (2014) 299-301 (5 pages).
Willan, A. R., et al., "Accounting for treatment by center interaction in sample size determinations and the use of surrogate outcomes in the pessary for the prevention of preterm birth trial: a simulation study," Trials, Jul. 2016 (8 pages).
Yuce, T., et al., "Pessary use in pregnant women with short cervix", J. Turk. Ger. Gynecol Assoc. Jan. 2016 (3 pages).
Martinelli, P. et al., "Cervical Pessary and Spontaneous Preterm Birth," Journal of American Medical Association, May 1, 2008 (2 pages).
Bayer, V.H., "Various New Aspects for Prevention and Therapy of Impending Premature Birth," Zentralblatt fur Gynakologie, vol. 99, Issue 9, pp. 547-551 [no English translation].
Prevention of Preterm birth in Twins with Short Mid-Trimester Cervical Length Less than 25MM-combined Treatment with Arabin's Cerclage Pessary and Intravaginal Micronized Progesterone Compared with Conservative Treatment, 2018 (5 pages) [no English translation].
Javert, O.S., et al., "Treatment of the incompetent cervix with the Hodge Pessary," Obstet. Gynecol. Aug. 28, 1966 (4 pages).
Gyselaers, W., et al., "Gestational hypertensive disorders show unique patterns of circulatory deterioration with ongoing pregnancy," www.physiology.org/journal/ajpregu At Washington University on Feb. 13, 2019 (51 pages).
Malinova, M., "Clinical treatment in Shorten Cervix" 2013 (10 pages) [no English translation].
"First year experience using arabin cervical pessary with intravaginal micronized progesterone for the prevention of preterm birth in patients with mid-trimester short cervix," (2014) [no English translation].

(56) References Cited

OTHER PUBLICATIONS

Arabin, B., et al., "Is treatment with vaginal pessaries an option in patients with a sonographically detected short cervix?", J. Perinat. Med. 31 (2003) pp. 122-133 912 pages).
Brun, S., "Cervical pessary and spontaneous preterm birth," Elsevier (2016) 45, 1324-1336 (13 pages) [no English translation].
Monfrance, M., et al., "Pessary placement in the prevention of preterm virth in multiple pregnancies: a propensity score analysis," Elsevier, vol. 197 (2016) 76-77 (6 pages).
Dunn, L.J, et al., "Maternal death following suture of an incompetent cervix during pregnancy", Am J Obstet Gynecol 1962:84:114.
Leduc, L., et al., "Successful treatment with the Smith-Hodge pessary of cervical incompetence due to defective connective tissue in Ehlers-Danlos syndrome", Am J Perinatol 1992:9:25-27.
Newcomer, J., "Pessaries for the treatment of incompetent cervix and premature delivery", Obstet Gynecol Surv 2000:55:443-448.
PCT Search Report and Written Opinion of corresponding PCT appl. No. PCT/US/2020/015789 dated May 20, 2020.

\* cited by examiner

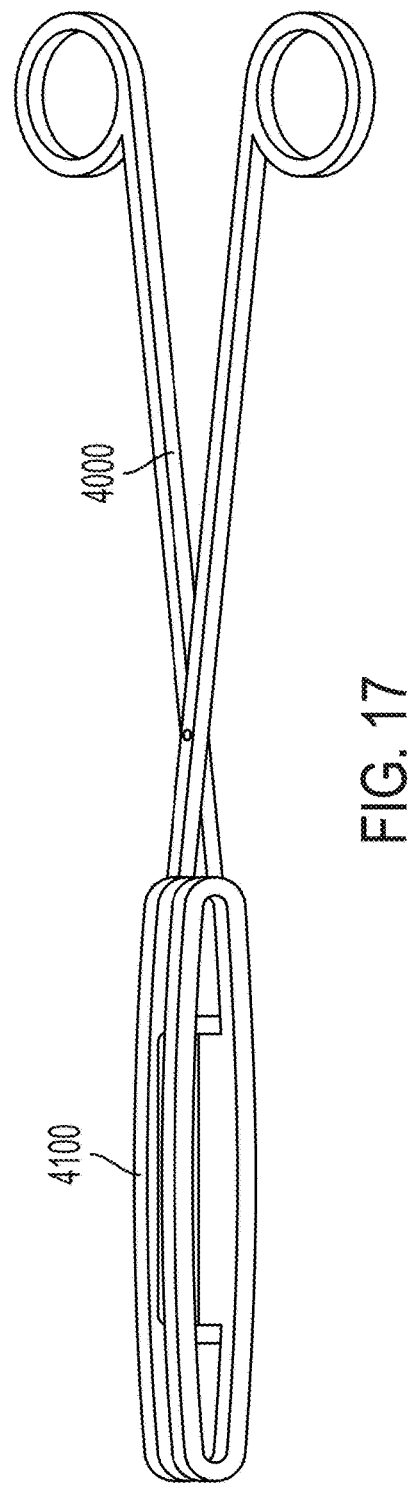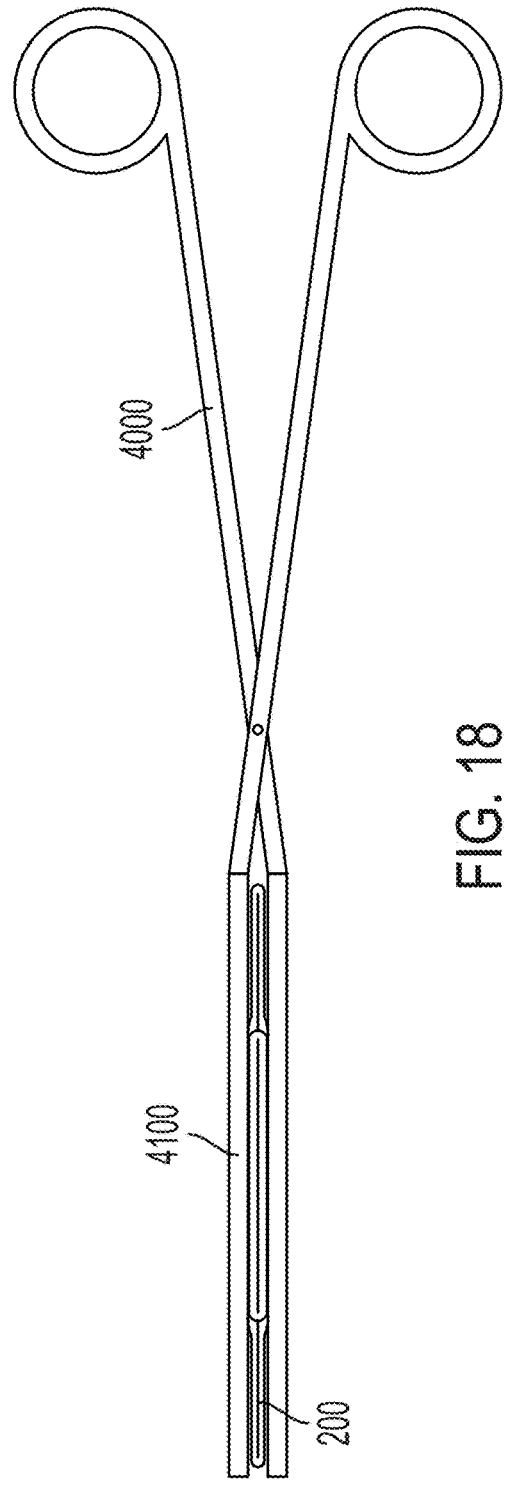

PESSARY DEVICE AND METHODS FOR PREVENTING PREMATURE BIRTHS

FIELD OF THE INVENTION

The present disclosure relates generally to a pessary device and methods for preventing premature births. More particularly, the present disclosure related to a pessary device for retaining the cervix during pregnancy to prevent premature births and associated methods.

BACKGROUND

Preterm birth (PTB) is the leading cause of perinatal morbidity and mortality in the United States. Despite efforts to decrease the incidence of this problem over the last few decades, the rate of preterm delivery remains high.

The PTB rate rose in 2017, and about 1 in 10 babies (10%) was born too early in the United States. Because of this high incidence, the prevention of preterm delivery is a major area of concern in contemporary obstetrics, as well as a societal necessity. According to the Centers of Disease Control (CDC) reducing PTB is a national public health priority.

Cervical Shortening and PTB

In 1996, it was demonstrated that the risk of preterm delivery is inversely proportional to the length of the cervix on transvaginal sonography between 24 and 28 weeks of gestation within an unselected United States population. (Jams J D, Goldenberg R L, Meis P J, et al: The Length of the Cervix and the Risk of Spontaneous Premature Delivery, N Engl J Med 1996:334:567-572)

Cervical insufficiency (formerly called "incompetence") as used herein means the inability of the uterine cervix to retain an intrauterine pregnancy until viability of the fetus. It is usually characterized as an acute, painless second trimester dilatation of the cervix resulting in premature delivery. A short cervix as used herein means a shortened anatomical length of the cervix as measured along the longitudinal axis of the cervix. It is usually found in the mid-trimester of the pregnancy and detected either by ultrasound or digital examination. A short cervix can be a hallmark finding used as a surrogate marker for diagnosis of cervical insufficiency. This is particularly relevant in those women with a previous history of pregnancy loss or preterm delivery. It has been appealing to clinicians to consider a mechanical method by which to strengthen the cervix, keep it closed, and increase its length in the hope of preventing preterm delivery.

Since the introduction of cerclage, or a cervical stitch, by Shirodkar (Shirodkar V N: *A New Method of Operative Treatment for Habitual Abortion in the Second Trimester of Pregnancy, Antiseptic* 1955:52:299) and McDonald (McDonald I A: *Suture of the Cervix for Inevitable Miscarriage, J Obstet Gynaecol Br Emp* 1957:64:712-714) in the 1950's, this treatment modality has been submitted to multiple study trials with mixed results. Furthermore, recently the use of progesterone for the treatment of a short cervix is also under intense research evaluation.

Cervical insufficiency and cervical shortening leading to preterm delivery are overlapping conditions in the spectrum of cervical shortening at various gestational ages. The distinction is sometimes difficult to make and is subjective.

Cervical Physiology

During the pregnancy the cervical canal normally stays tightly closed with a cervical mucus plug (CMP) filling its lumen. It is hypothesized that impairment of the CMP, for example, by cervical shortening, can lead to an ascending infection and preterm delivery.

Pessaries

As used herein, a pessary is a removable device placed into the vagina for therapeutic purposes. Pessaries currently come in a wide range of shapes and sizes and are typically used for pelvic organ prolapse. Typically, they are of a ring-like shape which circumscribes the cervix and performs similar to a cerclage. (See, McDonald)

The thought behind the mechanism of action of the pessary was proposed by Vitsky in 1961. He described the pregnancy as causing a steady and mounting pressure on the internal orifice of the cervix ("internal OS") and noted that it is irrelevant whether this is due to cervical trauma or congenital causes. (Vitsky M: *Simple Treatment of the Incompetent Cervical Os, Am J Obstet Gynecol* 1961:81: 1194-1197). The pattern is the same, and eventually the membranes weaken by sacculation and rupture, and, in due time, labor with expulsion of the uterine contents. The cervix with its axis directly and centrally aligned into the non-resistant vagina, lends itself to its own dissolution. Vitsky suggested that a device that can alter this collineation so that the force is directed inward would be helpful. He suggested that a pessary might have merit in this situation, as it can change the inclination of the cervical canal and can also compress the cervical canal in the earlier part of pregnancy.

Pessaries for the Prevention of PTB

Early reports on the use of pessaries for the prevention of spontaneous PTB (sPTB) used models originally designed to treat genital prolapse.

In 1959, Cross described his experience using a ring pessary in 13 patients with either a history of cervical lacerations, cervical incompetence or uterus didelphus. (Cross R. G: *Treatment of Habitual Abortion due to Cervical Incompetence, Lancet* 1959:2:127) Vitsky described the use of a Hodge pessary in seven patients and in a further 14 of his colleagues' patients, postulating that the reduction of pressure on the internal os prevented the protrusion of membranes. (Vitsky M. *Simple treatment of the incompetent cervical os. Am J Obstet Gynecol* 1961; 81:1194). He also suggested that a pessary might change the inclination of the cervical canal and compress the cervix, but this was never tested. Considering the large openings of the Hodge and ring pessaries, this hypothesis does not seem likely. Oster and Javert also used a Hodge pessary in 29 patients with 'cervical incompetence' defined by different criteria, arguing that treatment with a pessary would be superior to surgical cerclage due to the reduced risk of bleeding or maternal sepsis. (Oster S, Javert C. T. *Treatment of the Incompetent Cervix with the Hodge Pessary, Obstet Gynecol* 1966:28: 206-208). The Hodge pessary encompasses the cervix and compresses the cervical canal, and as such may prevent the loss of the CMP. The pessary also alternates the inclination of the cervical canal and corrects the incompetent cervix pointing forward in the axis of the vagina. It relieves direct pressure on the internal OS by distributing the weight of the pregnant uterus onto the vaginal floor, the retro-symphyseal osteomuscular structures, and the Douglas cavity and, as such, may prevent premature dilatation of the cervix and premature rupture of the membranes. Furthermore, it blocks the fetal head from descending and pressing on the internal ostium (a/k/a internal orifice or internal os).

The cervical pessary is relatively noninvasive and is not an operator-dependent intervention. It can be easily placed or removed in an outpatient clinic and does not require anesthesia. With speculum examination, the cervix is identified to determine an appropriate pessary size. The silicon Arabin pessary, available for example from Dr. Arabin GmbH & Co. KG of Witten Germany as the Cerclage and Cerclage Perforated Pessary models, are popular and come in different sizes of diameter and height. They are non-collapsible with limited bending and fit high around the cervix so that smaller inner diameter of the prior art ring structure encompasses or circumscribes the cervix. After placement the patient is briefly observed to ensure there is no discomfort, vaginal bleeding, or uterine activity.

Recent meta-analysis of the randomized trials identified six trials evaluating the use of pessary with cervical length (CL)<25 mm (1,992 using pessary devices vs 999 controls). Four trials administrated vaginal progesterone to the pessary and the control group. There were no significant differences seen in the rates of spontaneous PTB (sPTB) or any PTB prior to 28, 34, or 37 weeks. There was high heterogeneity noted for sPTB<34 weeks. Three trials found no significant reduction in sPTB rate<34 weeks, while two trials demonstrated a significant reduction (6.3% vs 26.8%; 7.3% vs 15.3%, respectively). (Liem S M et al. *Cervical pessaries for the prevention of preterm birth. A systematic review.* Obstetrics and Gynecology International 2013; 2013 Article 576723). Women with pessaries were more likely to report increased vaginal discharge at follow up visits. Only 5.4% requested removal of the pessary. There were no significant differences in delivery or neonatal outcomes. Based on single gestations with short cervical length randomized to cervical pessary, the investigators concluded that there was not a significant difference in rates of PTB between the pessary group and the control group. However, these results demonstrate the large heterogeneity in both the statistical analysis as well as in the results of individual trials.

Thus, there are certain shortcomings of the prior art pessary devices. First, the need exists for an improved pessary that serves to extend the length of the cervix in women at risk of preterm pregnancies. There is also a need to configure the pessary so that degradation of vaginal flora is minimized thereby decreasing the chances of infection within the birth canal during gestation and at birth. Further, an improved pessary is needed to retain, and preferably enhance, the radial forces on the circumscribed cervix when the patient is standing. Moreover, the pessary should be made of a biologically compatible, pliable, collapsible and consistent material which maximizes the ease of installation, retention and removal. All this should be done while continuing to maximize patient comfort.

It should be understood that the above-described features, capabilities and disadvantages are provided for illustrative purposes only and are not intended to limit the scope or subject matter of the appended claims or those of any related patent application or patent. Thus, none of the appended claims or claims of any related application or patent should be limited by the above discussion or construed to address, include or exclude each or any of the above-cited features, capabilities or disadvantages merely because of the mention thereof herein.

BRIEF SUMMARY OF THE DISCLOSURE

The present disclosure is a pessary used to prevent premature birth of a fetus and, in particular, two pathological conditions of pregnancy known as isthmico-cervical insufficiency and cervical shortening, both of which are associated with increased risks for pregnancy loss and/or premature deliveries of babies.

The pessary of the present disclosure comprises a hollow, open-ended sleeve configured to circumscribe the cervix. At the top or superior end of the sleeve the pessary includes an annular member having a superior surface and an inferior surface. The superior surface of the annular member engages the vagina proximate the cervix. The pessary further includes a ring attached at the outer edge of the annular member which also engages the vagina. In this manner, upon final placement of the pessary within the vagina at least a portion of the interior surface of the sleeve contacts a portion of the cervix and at least a portion of the superior surface of the annular member and at least a portion of the outer surface of the ring contact a portion of the vagina. This configuration serves to lengthen the cervix.

In another embodiment of the present disclosure the sleeve, annular member, and ring include a plurality of apertures which provide fluid communication throughout the pessary in order to permit hydration of the cervix and vagina and drainage of vaginal discharge resulting from epithelial turnover.

In yet another embodiment of the present disclosure, the longitudinal length of the sleeve is greater than the longitudinal length of the ring. Preferably, the longitudinal length of the sleeve is at least 50% greater than the longitudinal length of the ring, and more preferably, the longitudinal length of the sleeve is at least twice the longitudinal length of the ring.

In a further yet embodiment of the present disclosure, the pessary includes at least one sensor preferably mounted proximate the sleeve and in contact with the cervix. In this manner, the sensor may receive a signal indicative of a physiological condition such as premature contraction. It may also be configured to generate a signal, for example, such as an electrical current to inhibit the premature contractions of the uterus.

In yet a further embodiment of the present invention, portions of the pessary such as the sleeve, annular member, and/or the ring may include a coating of a biologically beneficial medication, such as progesterone, prostaglandin inhibitors and other beneficial drugs. Alternatively, the pessary may be manufactured of the material comprising the medical-grade polymeric material such as silicone and/or polyurethane impregnated with biologically beneficial medication which is intended for slow release onto the cervix or within the vagina and/or uterus.

Accordingly, the present disclosure includes features and advantages which are believed to enable it to advance medical technology. Characteristics and advantages of the present disclosure described above, and additional features and benefits will be readily apparent to those skilled in the art upon consideration of the following detailed description of various embodiments and referring to the accompanying drawings.

BRIEF DESCRIPTION OF THE DRAWINGS

The following figures are part of the present specification, included to demonstrate certain aspects of various embodiments of this disclosure and referenced in the detailed description herein:

FIG. 17 is an isometric view of alternative forceps used to compress the present invention in the alternative configuration shown in FIG. 16.

FIG. 18 is an isometric view of the present invention compressed in the alternative flat configuration of FIG. 16 by the alternative forceps shown in FIG. 17.

DETAILED DESCRIPTION OF PREFERRED EMBODIMENTS

Figure 1:
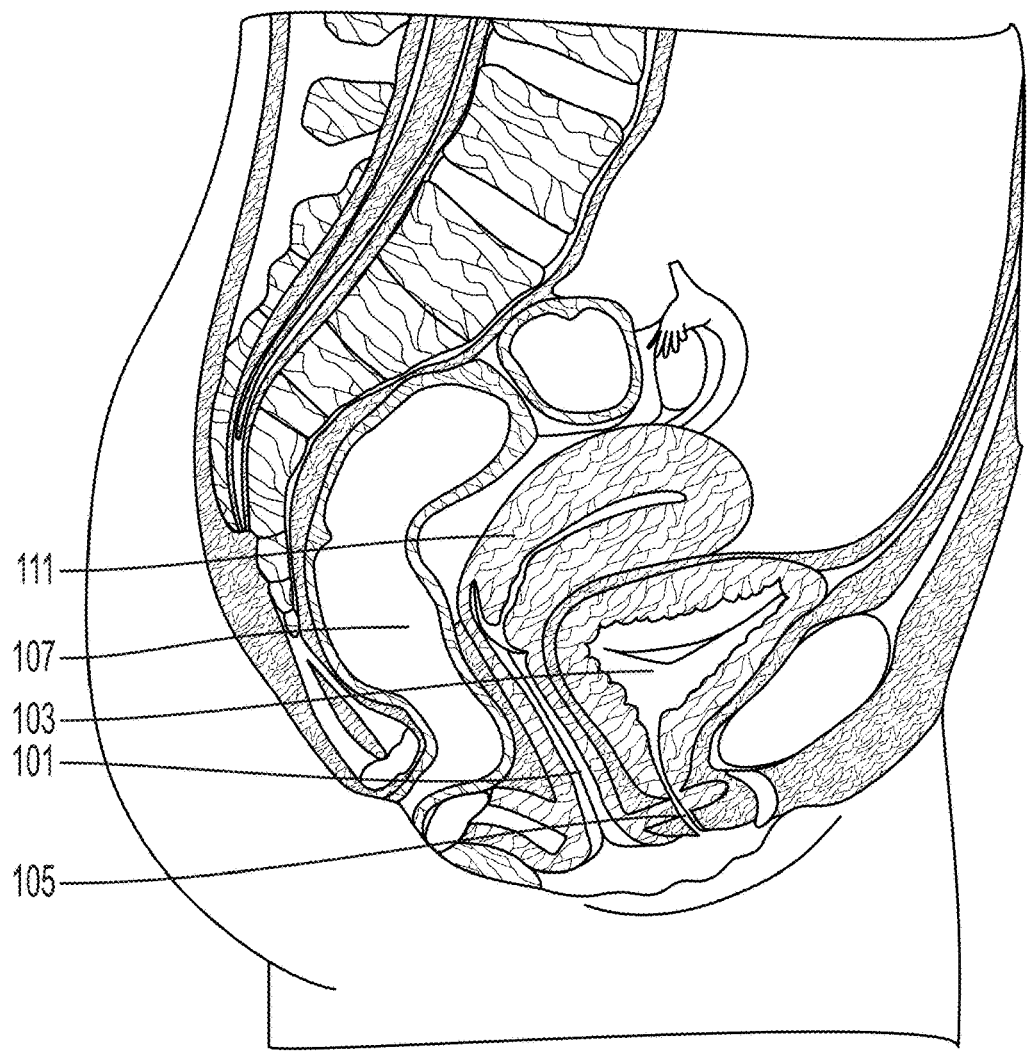
FIG. 1 is an anatomical view of the abdominal portion of a normal female.

The present invention now will be described more fully hereinafter with reference to the accompanying drawings, in which at least some preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Characteristics and advantages of the present disclosure and additional features and benefits will be readily apparent to those skilled in the art upon consideration of the following detailed description of exemplary embodiments of the present disclosure and referring to the accompanying figures. It should be understood that the description herein and appended drawings, being of example embodiments, are not intended to limit the claims of this patent application or any patent or patent application claiming priority hereto. On the contrary, the intention is to cover all modifications, equivalents and alternatives falling within the spirit and scope of this disclosure or any appended claims. Many changes may be made to the particular embodiments and details disclosed herein without departing from such spirit and scope.

In showing and describing preferred embodiments in the appended figures, common or similar elements are referenced with like or identical reference numerals or are apparent from the figures and/or the description herein. The figures are not necessarily to scale and certain features and certain views of the figures may be shown exaggerated in scale or in schematic in the interest of clarity and conciseness.

As used herein and throughout various portions (and headings) of this patent application, the terms "invention", "present invention" and variations thereof are not intended to mean every possible embodiment encompassed by this disclosure or any particular claim(s). Thus, the subject matter of each such reference should not be considered as necessary for, or part of, every embodiment hereof or of any particular claim(s) merely because of such reference. The terms "coupled", "connected", "engaged", "attached", and the like, and variations thereof, as used herein and in the appended claims are intended to mean either an indirect or direct connection or engagement. Thus, if a first device couples to a second device, that connection may be through a direct connection, or through an indirect connection via other devices and connections.

Certain terms are used herein and in the appended claims to refer to particular components. As one skilled in the art will appreciate, different persons may refer to a component by different names. The use of a particular or known term of art as the name of a component herein is not intended to limit that component to only the known or defined meaning of such term (e.g. bar, member, connector, rod, cover, panel, bolt, screw, and pin). Further, this document does not intend to distinguish between components that differ in name but not function. Also, the terms "including", "comprising", and "having" are used herein and in the appended claims in an open-ended fashion, and thus should be interpreted to mean "including, but not limited to . . . ." Further, reference herein and in the appended claims to components and aspects in a singular tense does not necessarily limit the present disclosure or appended claims to only one such component or aspect, but should be interpreted generally to mean one or more, as may be suitable and desirable in each particular instance.

As used herein, the terms "elongated" and variations thereof mean having an average length that is greater than its average width. As used herein, the terms "substantially", "generally" and variations thereof means and includes (i) completely, or 100%, of the referenced parameter, variable or value, and (ii) a range of values less than 100% based upon the typical, normal or expected degree of variation or error for the referenced parameter, variable or value in the context of the particular embodiment or use thereof, such as, for example, 90-100%, 95-100% or 98-100%.

Figure 2:
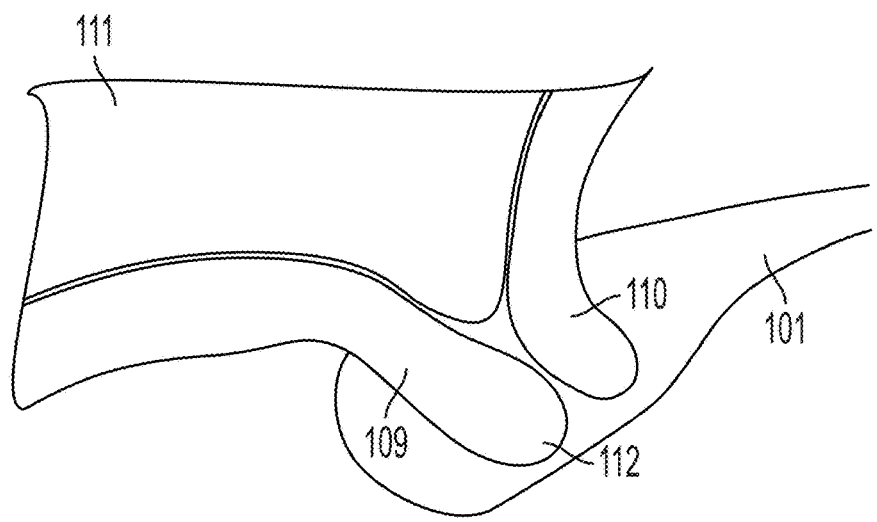
FIG. 2 is a simplified anatomical schematic of a cervix extending from a uterus into a vagina.

Referring to FIG. 1, a cross-sectional female abdominal sketch is shown. Vagina 101 is shown relative to bladder 103, urethra 105, and rectum 107. Referring now also to FIG. 2, cervix 109 is positioned descended from uterus 111. As noted above, while a cervical pessary is a relatively noninvasive, the present invention is pliable, collapsible, elastic, and self-expandable conserving its original shape. In addition, the present invention conforms to the anatomy of the cervix 109 proximate to bladder 103, urethra 105 and rectum 107. These properties facilitate placement and ensure patient comfort during retention around the cervix.

Figure 3:
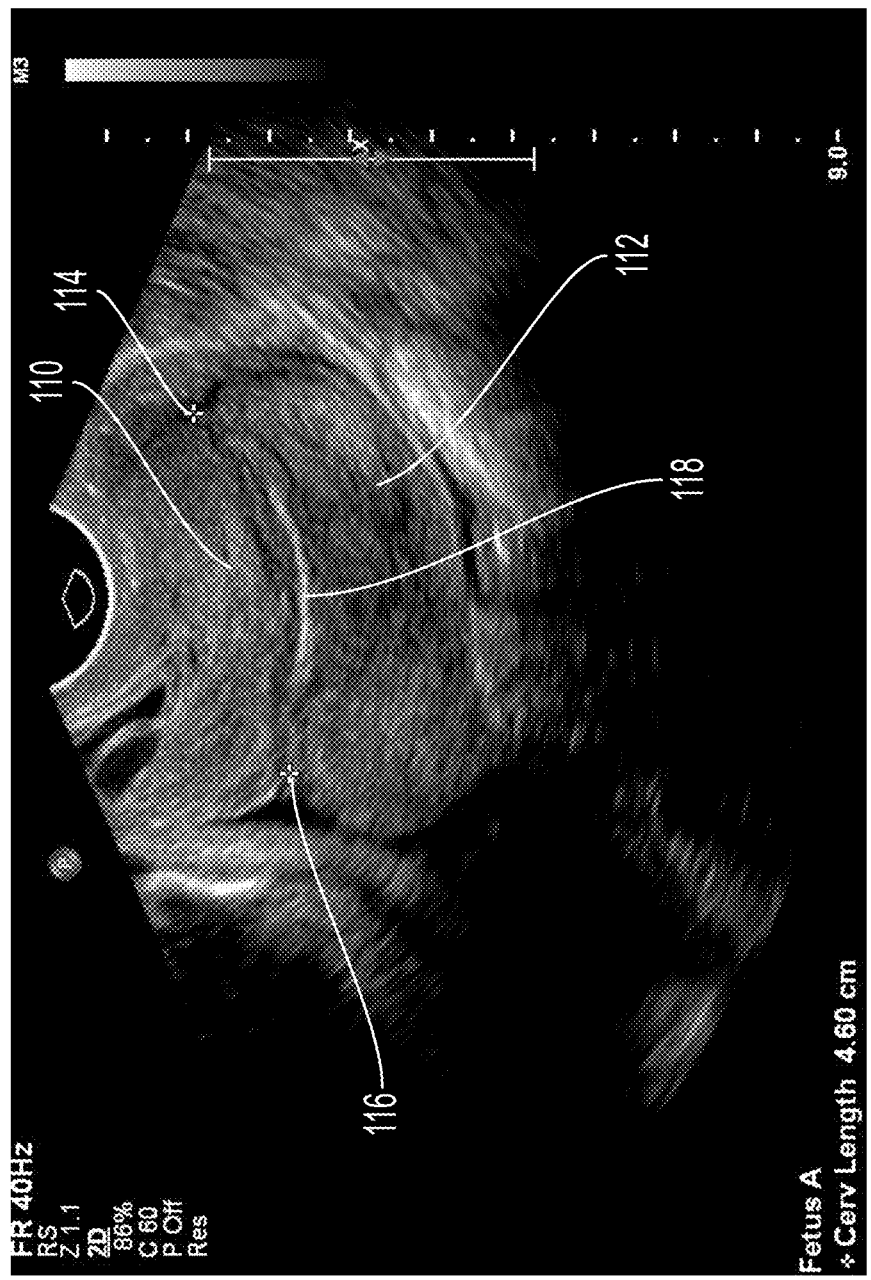
FIG. 3 is an ultrasound of a normal cervical anatomy.

Referring to FIG. 3, an ultrasound of a normal cervical anatomy is shown. Cervix 109 comprises an anterior lip 110 and a posterior lip 112. The external orifice (EOS) 114 and internal orifice (IOS) 116 of the of the uterus wall are also identified. Endocervical canal 118 is shown between anterior lip 110 and posterior lip 112.

Figure 4:
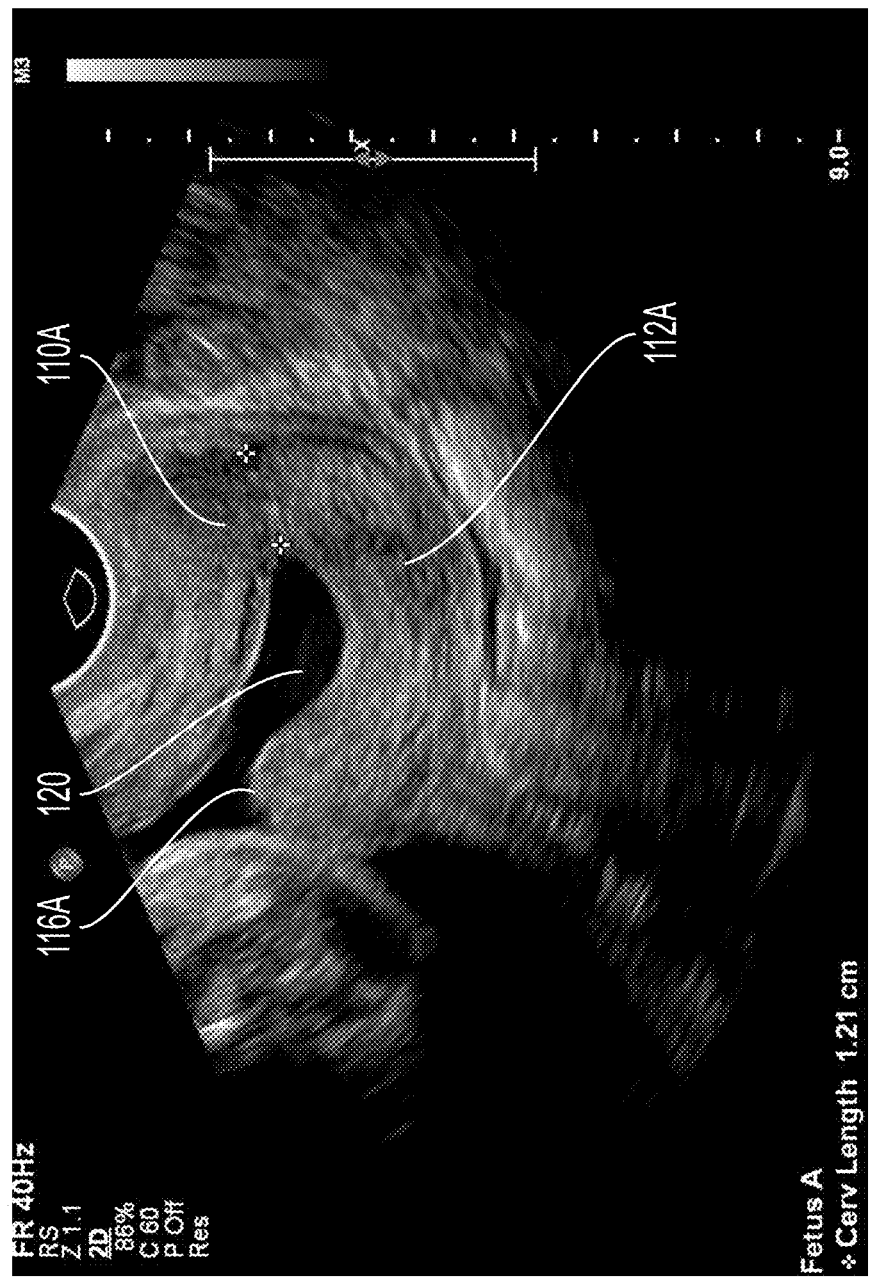
FIG. 4 is an ultrasound of a shortened anatomical cervix.

Referring now to FIG. 4, an ultrasound of an abnormally short cervix is shown having an anterior lip 110A displaced from posterior lip 112A resulting in an internal funnel 120 of the proximate the internal OS 116A. Such a funnel 120 results in a shortening of the cervix which is inversely proportional to the length of funnel 120. That is, the longer the length of funnel 120, the shorter the length of the cervix.

Figure 5:
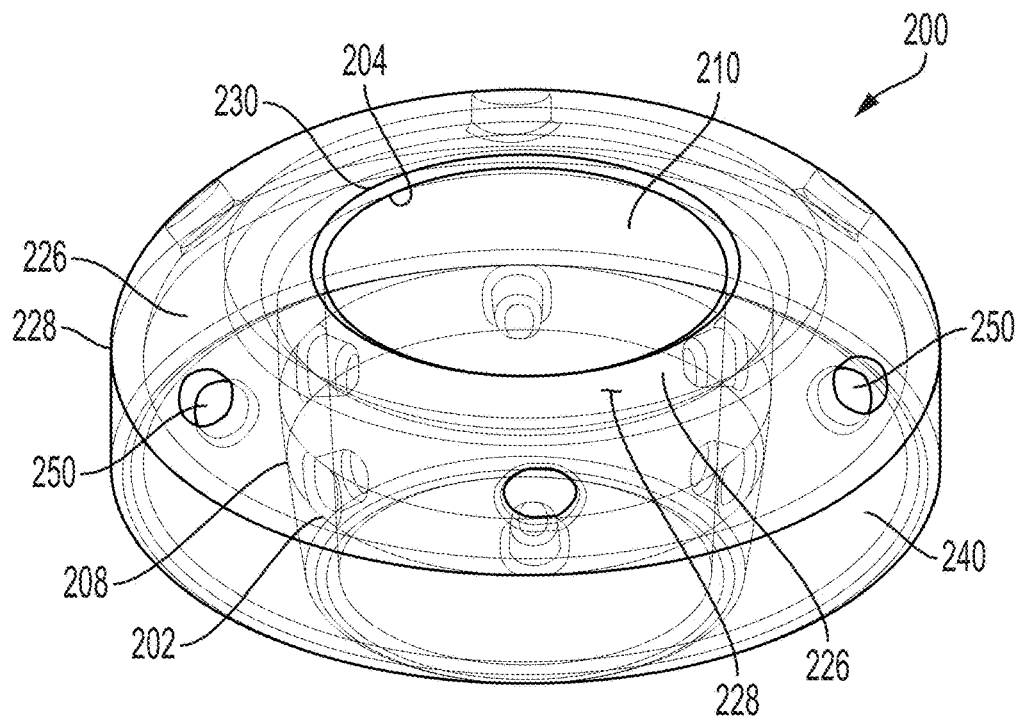
FIG. 5 is an isometric view of the superior side of the present invention.
Figure 6:
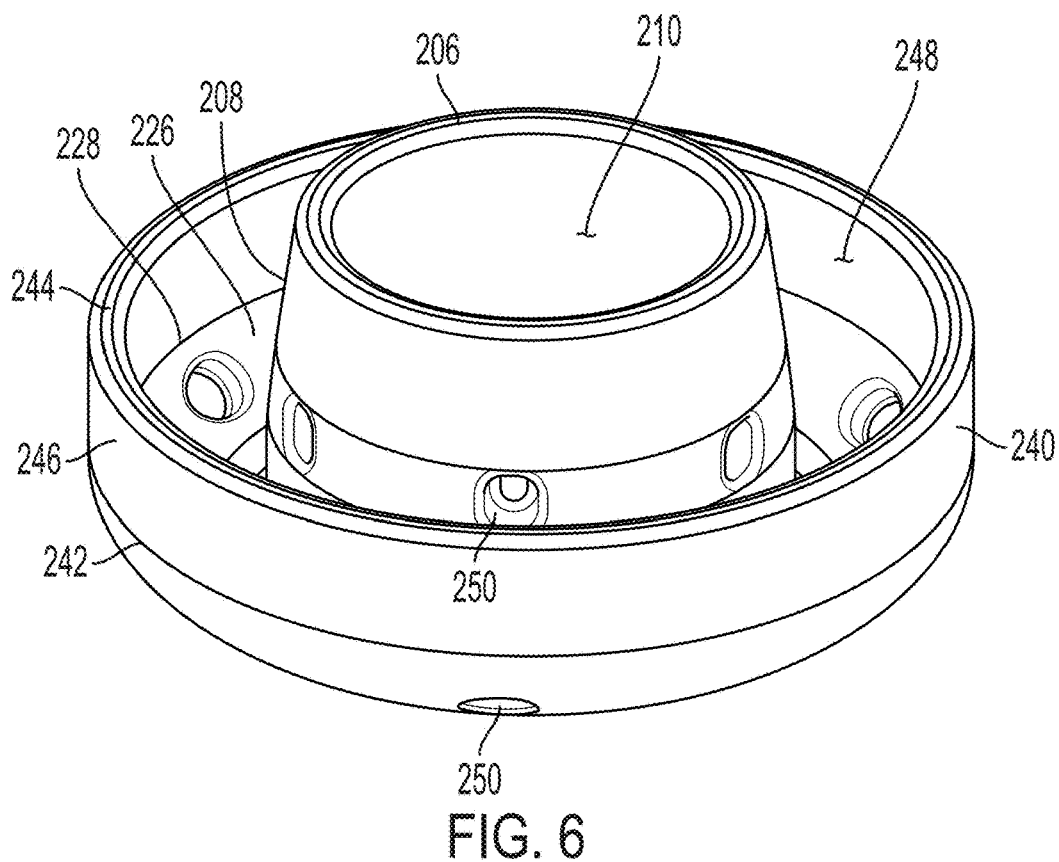
FIG. 6 is an isometric view of the inferior side of the present invention.
Figure 7:
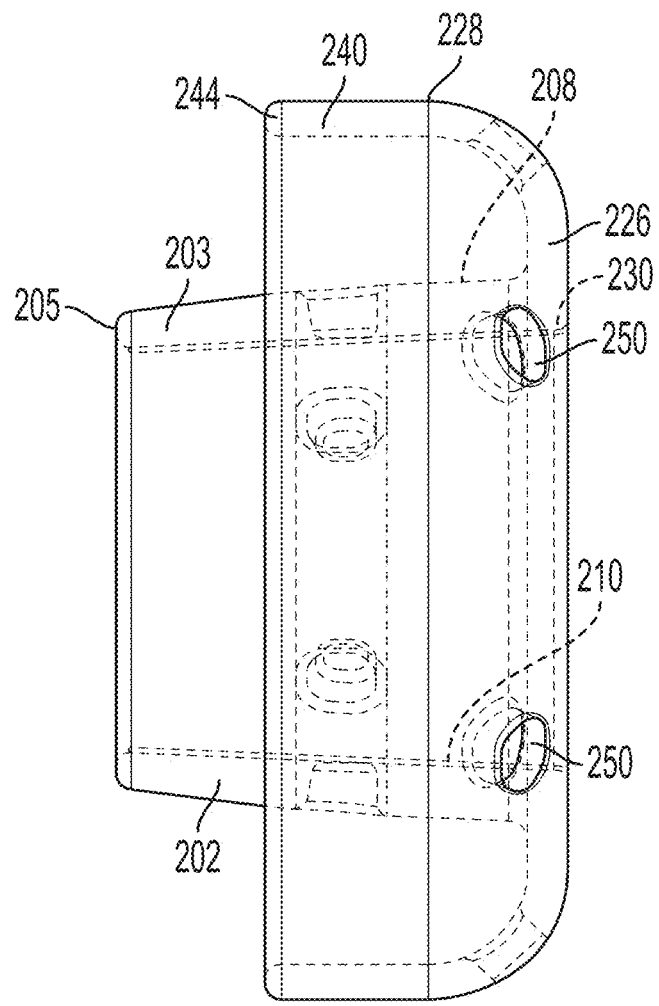
FIG. 7 is a side view of the present invention.

Referring to FIGS. 5-7, the present invention comprises a pessary device 200 having an internal sleeve 202 having a first edge 204, a second edge 206, an outer surface 208 and an interior surface 210. The present invention also includes an annular member or portion 226 having an outer edge 228 and an inner edge 230. Sleeve 202 is supported by annular member 226 at first edge 204 by inner edge 230 of annular member 226. The present invention also includes a ring 240 having first edge 242, a second edge 244, an outer surface 246 between the first and second edges 242/244, and an interior surface 248 between edges first and second edges 242/244. First edge 242 of ring 240 is attached to outer edge 228 of annular member 226.

The length of sleeve 202 between first edge 204 and second edge 206 is preferably greater than the distance between first and second edges 242/244 of ring 242. More preferably, the length of sleeve 202 between first edge 204 and second edge 206 is at least 50% greater than the distance between first and second edges 242/244 of ring 242. Even more preferably, the length of sleeve 202 between first edge 204 and second edge 206 is at least 75% greater than the distance between first and second edges 242/244 of ring 242. Most preferably, the length of sleeve 202 between first edge 204 and second edge 206 is at least twice the distance between first and second edges 242/244 of ring 242.

Referring in particular to FIG. 7, wall 203 of sleeve 202 may be tapered slightly as shown, so that at least inner surface 210 tapers slightly inwardly toward the cervix once placed within a patient. The outer surface 208 may be tapered slightly inwardly as shown, particularly proximate edge 205. In this manner, the lower or inferior portion of wall 203 is slightly more pliable and may more easily grasp the posterior and anterior lips 110/112 of cervix 109 and retains same in place due the anatomy of the patient's cervix and the transmission of radial forces from the vaginal muscle as discussed below.

The present invention may include one or more apertures 250 which serve to prevent the accumulation of fluid and to allow for lubrication and hydration of the roof of the vaginal walls. Interior surface 210 of sleeve 202 contacts and circumscribes cervix 109 once installed in the patient. Apertures 250 passing through sleeve 202 serve to allow for lubrication and hydration of the cervix, and drainage of cellular debris. As interior surface 210 is intended to contact the outer portion of cervix 109, it transmits an elastic load to stabilize and occlude cervical canal 118. Interior surface 210 of sleeve 202 has more surface area than a simple ring-shaped prior art pessary device which thereby makes the present invention more effective in transmitting an elastic force to the cervix, and in supporting the cervix.

FIG. 5 shows the superior view of device 200 with dashed lines reflecting internal geometry. FIG. 6 is an inferior view of device 200, and FIG. 7 is a side view of device 200. Elements of the present invention are shown with similar numerals to reflect the same elements as discussed above.

Figure 8:
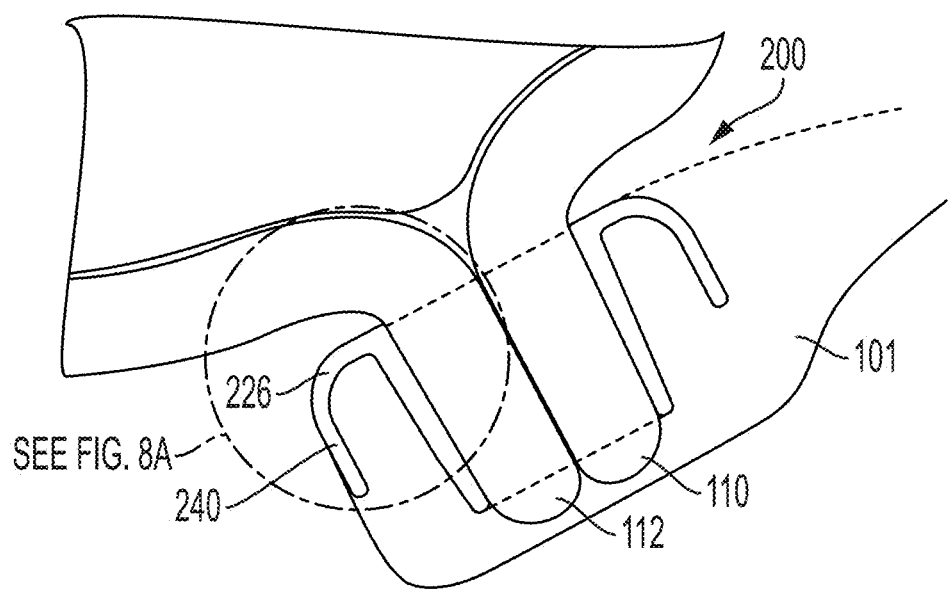
FIG. 8 is a sketch of the present invention in final position at a cervix within a vagina.
Figure 8A:
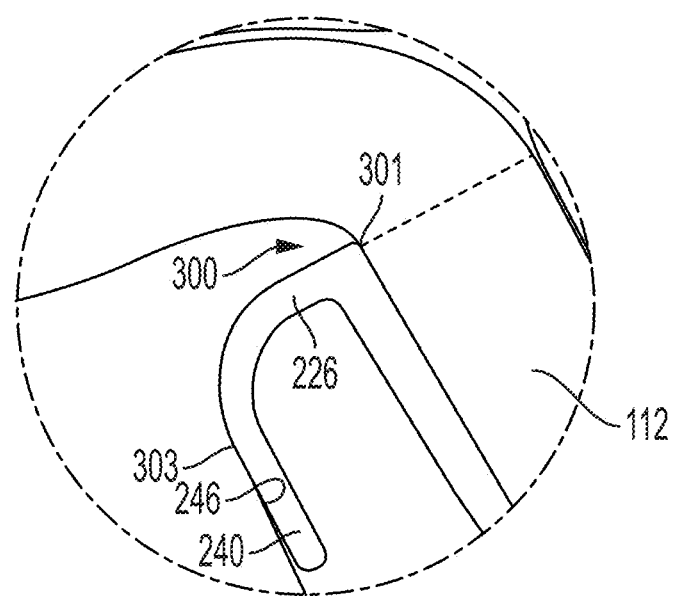
FIG. 8A is a detailed view of a portion of FIG. 8.

Referring now to FIGS. 8 and 8A, the shape of device 200 is selected so that annular member 226 contacts cervical vaginal interface 300 with upper convexity 301 of the shoulder of annular member 226. Thus, outer surface 246 of ring 240 fit snugly against the vaginal ceiling 303. This serves to provide additional support for device 200 and enhance patient comfort.

Figure 9:
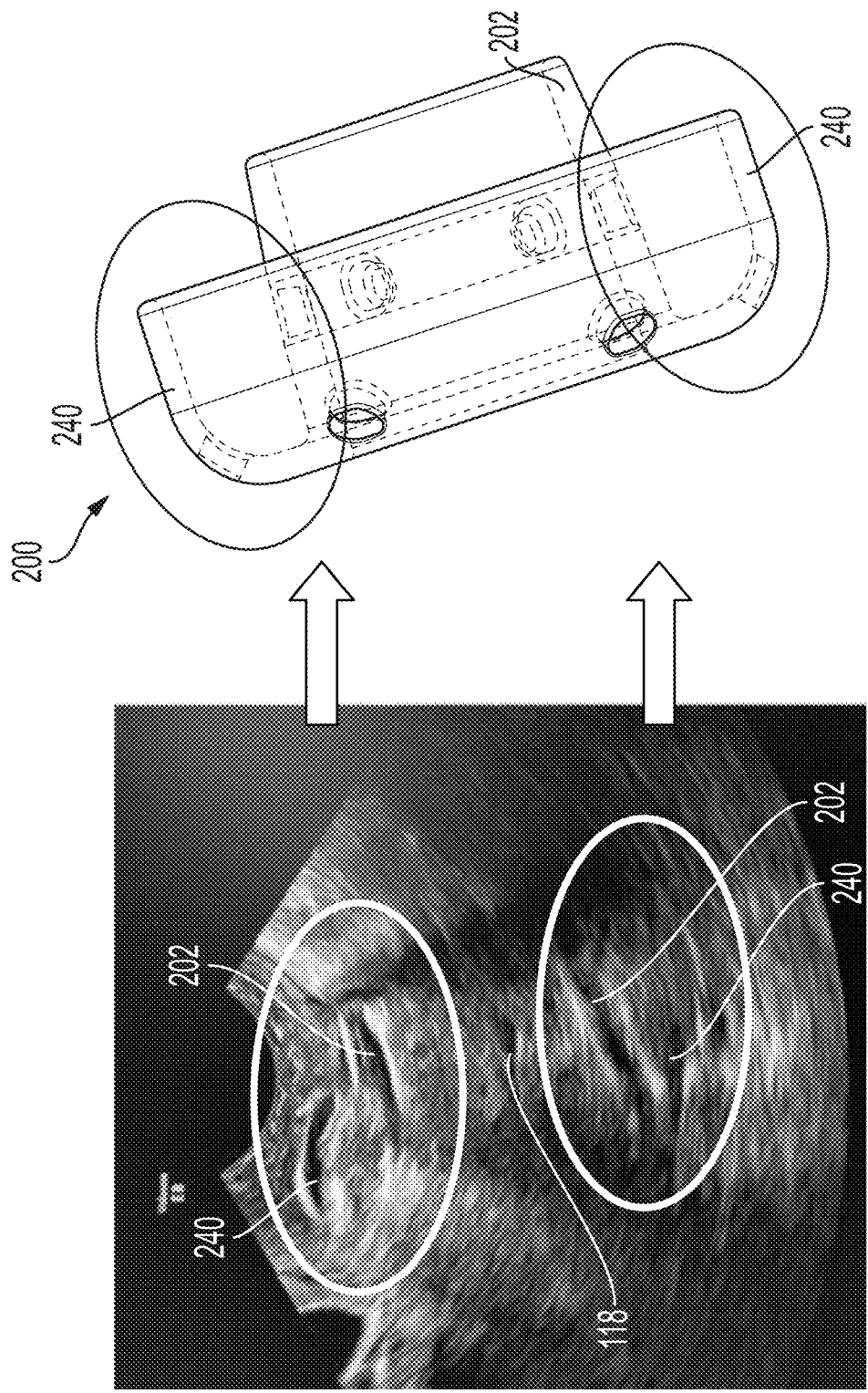
FIG. 9 is an ultrasound of the present invention in place circumscribing the cervix within the vagina.

Referring now to FIG. 9, an ultrasound is shown with device 200 inserted within the vagina and positioned about the cervix. Device 200 is shown as an echolucid structure positioned around the cervix and sleeve 202 and ring 240 are visible. This ultrasound shows an elongation of the cervical canal 118 after implantation of the present invention and resolution of amniotic membranes funneling.

The present invention stabilizes the relationship between cervix 109 and uterus 111 using the mechanical transmission of radial forces. In this manner, the present invention mechanically reinforces the cervical area of the uterus in order to stabilize, and/or to increase the longitudinal length of, the entire anatomical area, including the cervix. In normal circumstances the upright position of the patient results in greater hydrostatic pressure in the IOS and in a patient with cervical insufficiency, resulting in further cervical shortening. The present invention prevents the further shortening of the uterine cervical length when the patient is in an upright position. Such advantages serve to decrease the incidence of premature rupture of the membranes, one of the most common causes of premature babies. As such, the present invention is a new generation of cervico-vaginal pessary for the treatment of short cervices and cervico-isthmic insufficiency (also known as cervical incompetence).

Additionally, the present device stabilizes the cervix, elongates the cervical canal, decreases funneling and prevents further shortening of the cervix. These modifications of the cervical morphology are expected to be associated with decreased rates of preterm birth and its associated costs and complications.

Drug Eluting Applications

Figure 10:
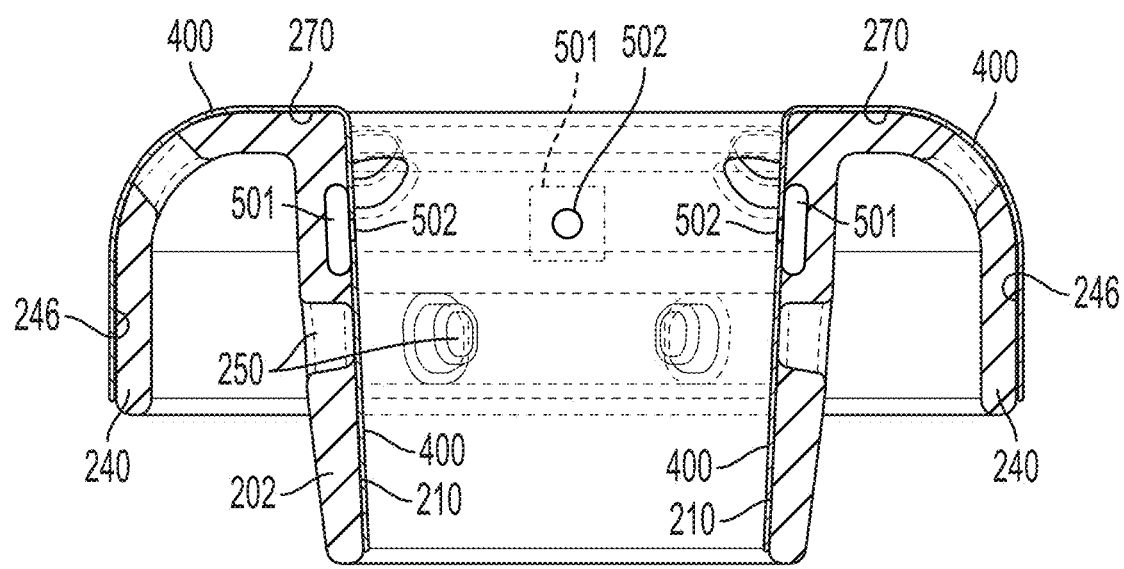
FIG. 10 is a view of an alternate embodiment the present invention.

Referring now to FIG. 10, an embodiment of the present invention is shown having a coating 400 applied to interior surface 210 of sleeve 202, superior surface 270 of annular member 226, and outer surface 246 of ring 240. While coating 400 is shown coating the interior surface 210 and surfaces 270 and 246, it may be preferable to only cover a portion of such surfaces, for example only interior surface 210 if the intent is to limit deliver of a medication or drug to cervix 109. Additionally, coating 400 may be located proximate apertures 250 which further serves to permit the drug or medication to easily transfer throughout device 200 and the vaginal and cervical region.

Coating 400 would typically comprise a drug eluting technology (a/k/a as "DE Technology" to one-skilled-in-the-art) for dispensing medication over a period of time for a specific application. For example, in the case of the present invention, a drug may be used in the coating which deliveries a predetermined amount over a given time to maintain the mother's cervical length and the homeostasis of the baby, such as the medication progesterone or prostaglandin inhibitors such as indomethacin. The eluting process may deliver drugs at a rate from 1 mg to 1000 mg daily. Progesterone is available, for example, from Ferring Pharmaceutical in Parsippany NJ Prostaglandin inhibitors such as indomethacin are available, for example, from G&W Laboratories, Inc. South Plainfield, NJ 07080

Typically, coating 400 is manufactured by mixing the medication with a polymer and applying it to the device 200 at the specified areas or throughout device 200. The coating is permitted to dry prior to installation in a patient.

Another alternative to the use of coating 400 is to impregnate the material used to manufacture the device with drug or medication to permit the medication to be released slowly over time. The medication may be mixed with the silicone or other gels or constituents used in preparing the source material at the time of manufacture of device 200.

Yet another alternative to the use of coating or impregnating the source material, may be to place the medication is a pellet or rod form within slots 501 of sleeve 202 of device 200 at the time of molding device 200 as shown in FIG. 10. Slots 501 are in fluid communication with the interior of sleeve 202 through ports 502 thereby allowing the medication to be in contact with the cervix.

Sensor Applications

As one skilled in the art realizes, parturition in mammals is preceded by two physiological phenomena: (1) increased excitability and (2) increased connectivity among the myometrial cells, changes which are reflected in an electrical myogram of the uterus. The uterus is a smooth muscle syncitium which contracts spontaneously and autonomously without the need for any neuronal control. It achieves this through the formation of gap junctions that interconnect the cells such that the action potentials propagate through the smooth muscle cells. The abnormal excitation of the uterus may be abolished with overriding currents in a similar fashion to other excitable tissues. Such physiological relationships permit the placement of various sensors to achieve preferred results as discussed below.

Figure 11A:
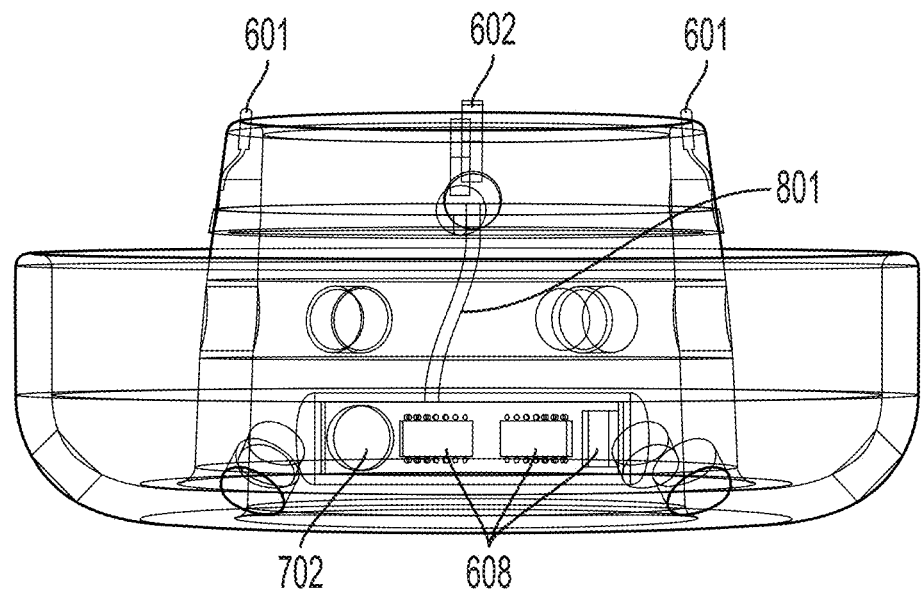
FIGS. 11A and 11B are views of yet another embodiment of the present invention.
Figure 11B:
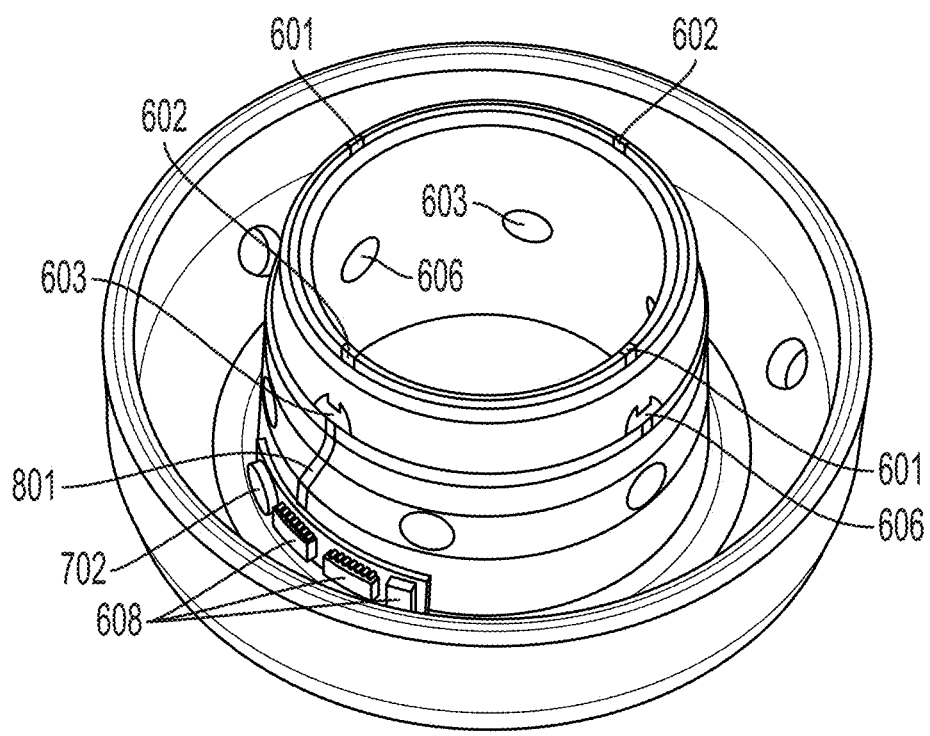
Figure 12:
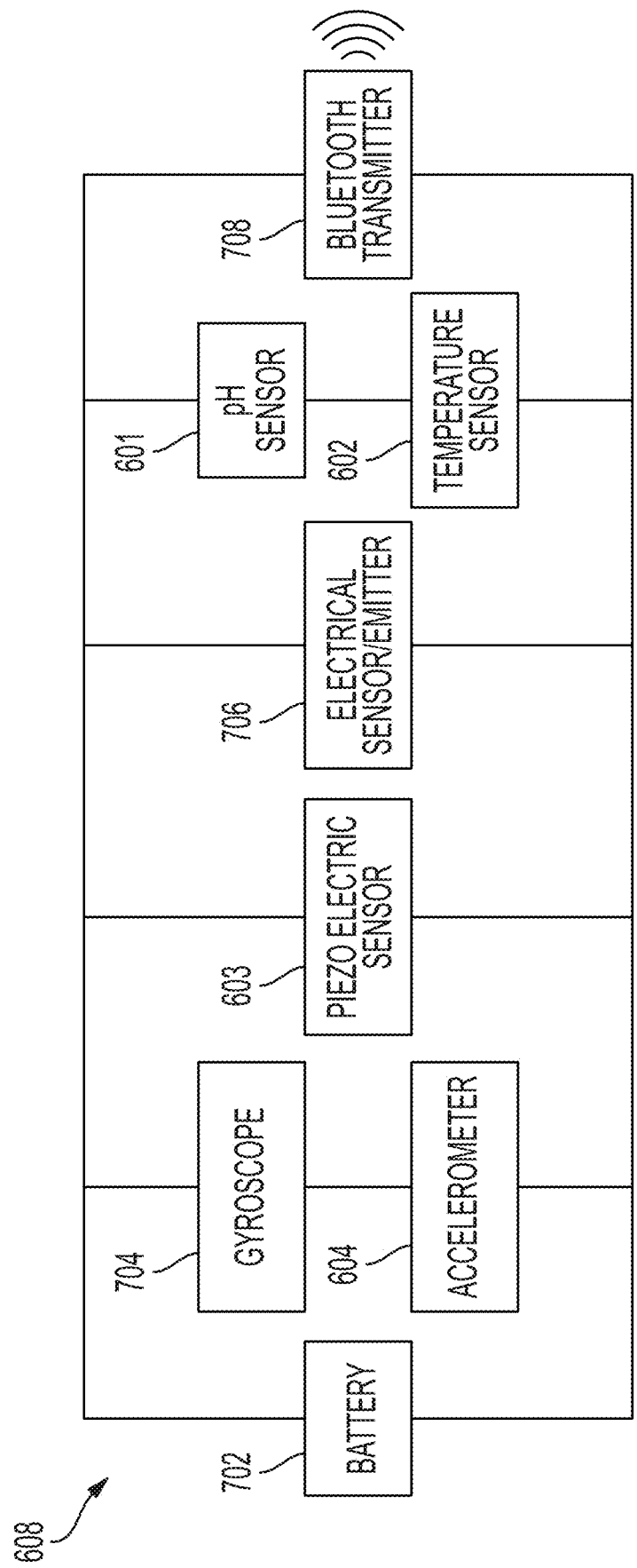
FIG. 12 is a schematic of the alternate embodiment of the present invention as shown in FIGS. 11A and 11B.

Referring now to FIGS. 11A, 11B and 12, an embodiment of the present invention is shown having various sensors which perform functions as described herein. Chemical meters 601 are positioned within the second edge 206 of sleeve 202. Meters 601 can capture change in the acidity or alkalinity of the cervix. The chemical receptors of meter 601 may detect pH changes that are transduced into voltages changes and then amplified using miniature transistors that transmit the voltage changes via Blue-tooth to a processing unit, such as an IOS device (iWatch or iPhone, for example) or Android based devices. There the signal can be further processed, for example, using a combination of filters, amplified and displayed as pH changes on a graphical user interface. An example of a suitable pH meter 601 is model LMP91200 available from Texas Instruments in Dallas, Texas http://www.ti.com/lit/ds/symlink/lmp91200.pdf Referring still to FIGS. 11A, 11B and 12, at least one temperature sensor 602 is embedded within member sleeve 202 to capture any change in the temperature of the cervix. Temperature changes are transduced into voltages changes that can be amplified using miniature transistors that transmit the voltage changes via Blue-tooth to a processing unit, such as an IOS device (iWatch or iPhone, for example) or Android based devices. There the signal can be further processed, for example, using a combination of filters, amplified and displayed as temperature changes on a graphical user interface. An example of a suitable temperature sensor 6012 is model 111-102CAJ-HO1 available from Honeywell International in Charlotte, North Carolina https://sensing.honeywell.com/111-102CAJ-H01-thermistors Referring still to FIGS. 11A, 11B, and 12, at least one piezoelectric sensor 603 is embedded within member sleeve 202 to capture any change in stress strain in the cervix. Excitation of the uterus causes voltages changes which can be amplified using miniature transistors that will be transmitted via Blue-tooth to a processing unit, such as an IOS device (iWatch or iPhone, for example) or Android based devices where the signal can be further processed and displayed as contractions as a function of time. An example of a suitable piezoelectric sensor 603 is model RS Pro 632146 available from Allied Electronics Automation in Fort Worth, Texas https://www.alliedelec.com Referring still to FIGS. 11A, 11B and 12, at least one accelerometer 604 is also embedded within circuitry 608 attached to sleeve 202. Accelerometer 604 captures any change in movement or displacement of cervix 109. Such movement or displacement changes are transduced into voltages changes that can be amplified using miniature transistors that transmit the voltage changes via Blue-tooth to a processing unit, such as an IOS device (iWatch or iPhone, for example) or Android based devices. In this manner the movement or displacement changes can be monitored. To supplement the reading of accelerometer 604, a gyroscope 704 (see FIG. 12) may be included which operates in conjunction with the accelerometer 604 to generate an orientation signal of the patient. An example of a suitable accelerometer 604 and gyroscope 704 is model LSM303 available from Adafruit Industries of New York, New York https://www.adafruit.com/product/1120

Referring still to FIGS. 11A, 11B and 12, at least one electric sensor and emitter 606 is shown having metallic unipolar and/or bipolar electrodes embedded within sleeve 202. Sensor/emitter 606 captures any changes in electrical currents. These currents are measured at the proximate level of the cervix in the form of electrical pulses or bursts which reflect increased electrical activity associated with a contraction and measured in millivolts. Once again, such electrical signals can be amplified using miniature transistors that transmit the voltage changes via Blue-tooth to a processing unit, such as an IOS device (iWatch or iPhone, for example) or Android based devices. Spectral and/or temporal parameters are handled with appropriate filters. In this manner, premature contractions may be measured. The physician may then, if desirable, attempt to stop the contraction by generating a signal from the processor back through the Blue-tooth connection to electrical circuitry 608 and, using battery 702, send a current to emitter 606 to interrupt the contraction. An example of a suitable sensor/emitter 606 model UA741CP available from Texas Instruments in Dallas, Texas http://www.ti.com/lit/ds/symlink/ua741.pdf With reference to FIG. 12, the electrical circuitry 608 is shown in schematic form having a battery 702 to power circuitry 608 and return a signal through meter 606 to attempt to interrupt a premature contraction. Circuitry 608 includes pH meter 601, temperature sensor 602, piezoelectric sensor 603, accelerometer 604, gyroscope 702, and voltage meter/emitter 606. Circuitry 608 also includes a Blue-tooth transmitter 708 The various sensors and meters may be connected within circuitry 608 by electrical connections or wires 801. In this manner, Blue-tooth transmitter 708 may communicate with a processing unit, such as an IOS device (iWatch or iPhone, for example) or Android based devices as described above, providing through a useful graphical interface, data helpful for the physician to evaluate the patient's condition and to evaluate the performance of the pessary device in preventing PTB. An example of a suitable Blue-tooth transmitter 708 is model TDK SESUB-PAN-D14580 available from TDK Corporation in Uniondale, New York https://product.tdk.com/en/search/rf/rf/module/info?part_no=SESUB-PAN-D14580

Additional modifications of the present invention as shown in FIGS. 11A, 11B, and 12 allowing for the detection of electrical, chemical, positional and temperature signals from the cervix and uterus by the detection of movement, temperature, pH changes, position and uterine contractile activity will be apparent by those skilled in the art based on this disclosure without altering the inventive concepts and principles embodied therein. The embodiments are therefore to be considered in all respects as illustrative and not restrictive, the scope of the invention being indicated by the appended claims rather than by the foregoing description, and all changes which come within the meaning and range of equivalency of the claims are therefore to be embraced therein Manufacturing As noted above, device 200 is preferably manufactured of a medical grade polymeric material, more preferentially a silicone or polyurethane with elastic properties that allows segmental compression of certain structures after implantation for maximum patient comfort. It should be inert and biologically compatible. Such medical gels are well known to those skilled in the art.

Device 200 may be manufactured from a mold created by a digital design using a 3D printer. The mold is then used to create a reverse casting for the final product, a process well known to those skilled-in-the-art. In this manner, device 200 may be manufactured as a unitary piece.

In order to provide the necessary pliable characteristics for ease of installation as discussed below, the thickness of sleeve 202 is between about 0.5 mm and about 5 mm, and preferably between about 0.8 mm and about 3 mm. Most preferably, sleeve 202 is about 2 mm in thickness.

Additionally, in order to provide the necessary pliable characteristics for ease of installation as discussed below, the thickness of annular member 226 is between about 0.5 mm and about 5 mm, and preferably between about 0.8 mm and about 3 mm. Most preferably, annular member 226 is about 2 mm in thickness.

Moreover, in order to provide the necessary pliable characteristics for ease of installation as discussed below, the thickness of ring 240 is between about 0.5 mm and about 5 mm, and preferably between about 0.8 mm and about 3 mm. Most preferably, ring 240 is about 2 mm in thickness.

In order to provide optimum hardness yet not inhibit pliability, the optimum hardness of device 200 is preferably between about 20 ShoreA and about 60 ShoreA, most preferably between about 30 ShoreA and about 50 ShoreA.

Patient Insertion

Figure 15:
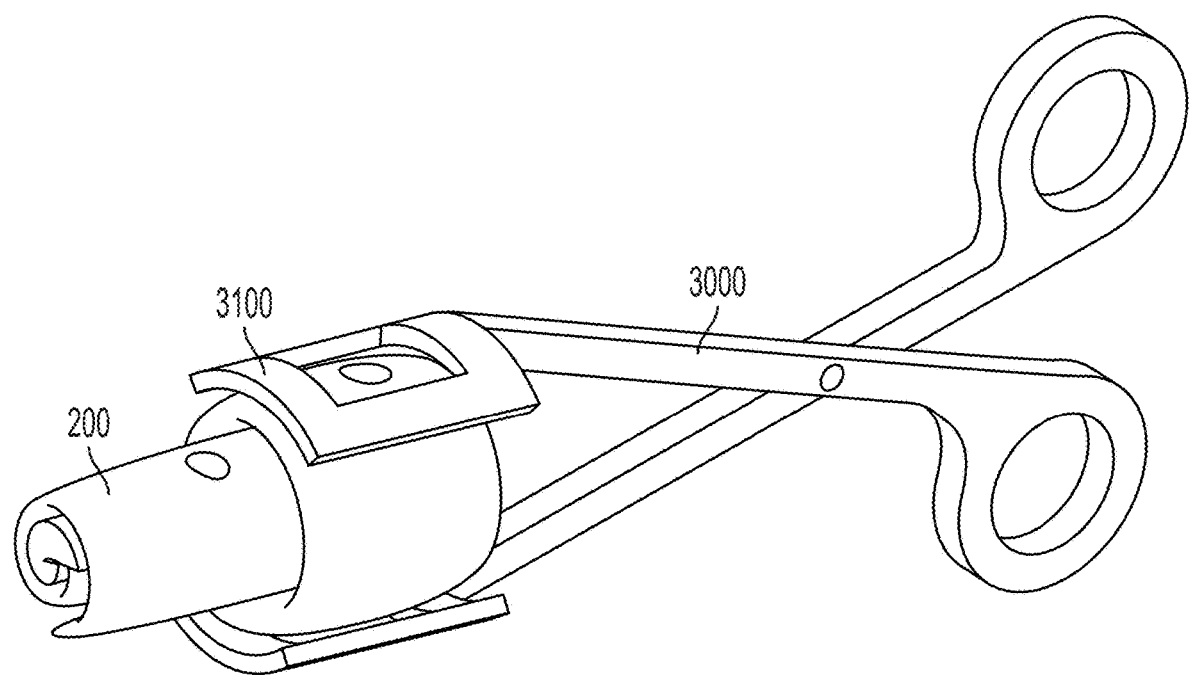
FIG. 15 is an isometric view of the present invention in a rolled configuration and being retained by curved forceps for insertion in a patient.
Figure 16:
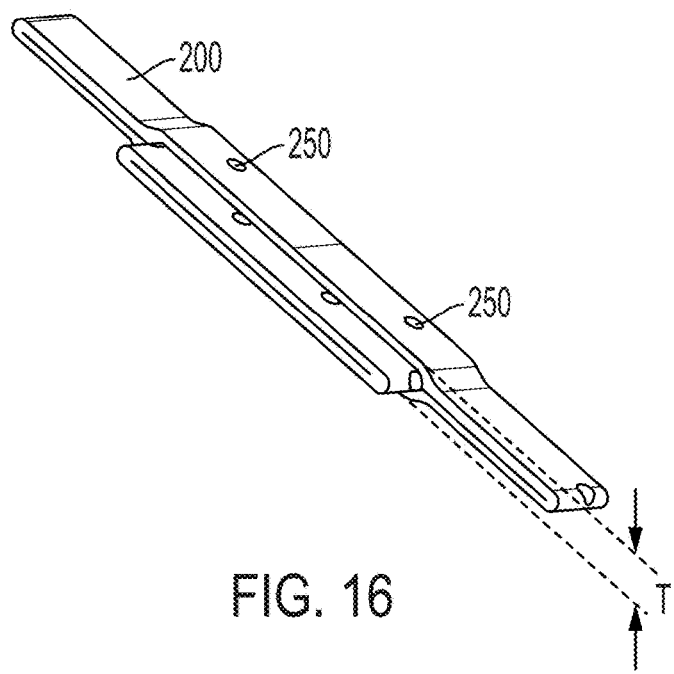
FIG. 16 is an isometric view of the present invention compressed flat as an alternative configuration prior to insertion in a patient.

Referring to FIGS. 13-18, device 200 is shown is a circular configuration (FIGS. 13-14) or in a compressed or flattened configuration (FIG. 16). Referring to FIG. 15, forceps 3000 having curved forks 3100 are used to secure device 200 when in a circular configuration for patient insertion. Alternatively, FIGS. 17-18 show forceps 4000 used to secure device 200 as shown in a flattened configuration (See FIG. 16). Forceps forks 4100 (See FIGS. 17-18) retain the flattened device 200 in the configuration shown in FIG. 16 for patient insertion.

In order to comfortable insert device 200 into the vagina and onto the cervix, device 200 may be compressed longitudinally as shown in FIG. 16 to a thickness "T" of no more than between about 4 mm and about 15 mm, and more preferably no more than about 8 mm. Also, referring to FIGS. 13 and 14, device 200 may be collapsed circumferentially to a circular diameter no more than between about 5 mm and about 40 mm, and more preferably no more than 29 mm.

The placement of a device 200 is simple and straightforward. Unlike the placement of regular pessaries, the present invention does not require sizing. Customization of the device is, nevertheless, possible once the physician knows the characteristics of the cervix per transvaginal ultrasound.

Placement of device 200 is possible under direct visualization or by digital exam.

Figure 13:
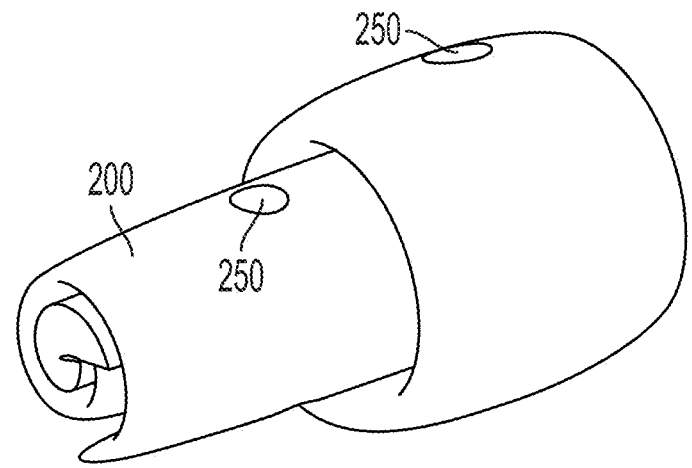
FIG. 13 is an isometric view of the present invention rolled prior to insertion in a patient.
Figure 14:
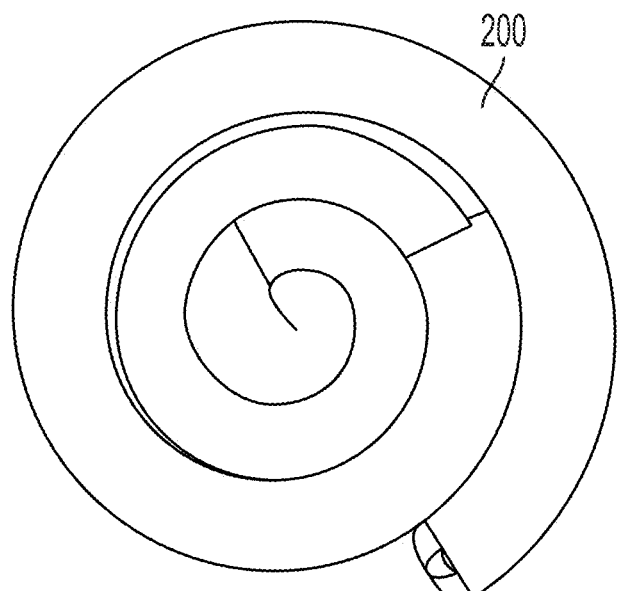
FIG. 14 is an end view of the present invention in a rolled configuration as shown in FIG. 13.

With respect to direct visualization, the following steps are preferably used in the placement of device 200 in the circular configuration shown in FIGS. 12-13 using direct visualization and forceps 3000 as shown in FIG. 15:

1. Have a chaperone.
2. Wear dry sterile gloves.
3. Place and secure a sterile speculum in the vagina to visualize the cervix.
4. Grasp device 200 using a ring forceps 3000, fold annular member 226 (bringing sides together) place ring 240 towards sleeve 202 and ring 240, bringing the sides together toward sleeve 202 and ring 240, resulting in the circular configuration shown in FIGS. 13-14.
5. Lubricate edge 228, ring 240, annular member 226, and surfaces 208 and 210 of sleeve 202 with a water-soluble lubricant.
6. Compress device 200 at the annular member 226 holding sleeve 202 toward the exterior.
7. Advance device 202 past the introitus with the dominant hand and allow device 202 to open into its final shape after passing the introitus.
8. Use the forceps 3000 guide device 202 past the cervix by gently push on the inner portion of annular member 226 advancing sleeve 202 around the cervix into the position shown in FIG. 8A.
9. Verify that the external OS is contained within sleeve 202 above at least the second edge 206 of sleeve 202.
10. While holding device 200 in place with the forceps 3000, unlock the speculum and start removing it while carefully observing final placement of device 200.
11. Remove the speculum.
12. After speculum removal ask the patient if she feels a foreign body. She should not.
13. May be helpful to get a transvaginal measurement of the cervical length at this time.

The following steps are preferably used in the placement of the present invention during a digital examination:

1. Have a chaperone.
2. Wear dry sterile gloves.
3. Lubricate surfaces 205 and 210 of sleeve 202 and surface 246 of ring 240 with a water-soluble lubricant.
4. Compress device 200 at the annular member 226 holding sleeve 202 toward the exterior.
5. Use one finger of the opposite hand to slightly depress the perineum.
6. Hold device 200 substantially parallel with the introitus.
7. Direct edge 228 past the introitus and allow device 200 to open into its final shape after passing the introitus.
8. Use the index and middle fingers to guide annular member 226 along the posterior vaginal wall into the posterior fornix until it does not advance any further.
9. Then use the index and middle fingers to guide the annular member 226 along the anterior vaginal wall into the anterior fornix until it does not advance any further thereby having placed sleeve 202 around the cervix into the position shown in FIG. 8A.
10. Verify that the external OS is contained within the sleeve 202 above at least the second edge 206 of sleeve 202.
11. Ask the patient if she feels a foreign body. She should not.
12. You may want to get a transvaginal measurement of the cervical length at this time.

Due to the snug retention of the cervix within sleeve 202, device 200 also serves to further wedge the patient's cervix within sleeve 202 when the patient is standing. The weight of the pregnant uterus onto the cervix and in turn device 200 may prevent premature dilatation of the cervix and premature rupture of the membranes. Furthermore, device 200 blocks the fetal head from descending and pressing on the internal ostium. This is a further advantage of device 200 in retaining the fetus and preventing PTB.

Having thus described in detail a preferred selection of embodiments of the present invention, it is to be appreciated and will be apparent to those skilled in the art that many physical changes could be made in the apparatus without altering the inventive concepts and principles embodied therein. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein

Preferred embodiments of the present disclosure thus offer advantages over the prior art and are well adapted to carry out one or more of the objects of this disclosure. However, the present invention does not require each of the components and acts described above. Any one or more of the above components, features and processes may be employed in any suitable configuration without inclusion of other such components, features and processes. Moreover, the present invention includes additional features, capabilities, functions, methods, uses and applications that have not been specifically addressed herein but are, or will become, apparent from the description herein, the appended drawings and claims.

The methods that may be described above or claimed herein and any other methods which may fall within the scope of the appended claims can be performed in any desired suitable order and are not necessarily limited to any sequence described herein or as may be listed in the appended claims. Further, the methods of the present invention do not necessarily require use of the particular embodiments shown and described herein, but are equally applicable with any other suitable structure, form and configuration of components.

While exemplary embodiments of the invention have been shown and described, many variations, modifications and/or changes of the system, apparatus and methods of the present invention, such as in the components, details of construction and operation, arrangement of parts and/or methods of use, are possible, contemplated by the patent applicant(s), within the scope of any appended claims, and may be made and used by one of ordinary skill in the art without departing from the spirit or teachings of the invention and scope of this disclosure and any appended claims. Thus, all matter herein set forth or shown in the accompanying drawings should be interpreted as illustrative, and the scope of the disclosure and any appended claims should not be limited to the embodiments described and shown herein.

What is claimed is:

1. A pessary device to prevent the preterm birth of a fetus through the cervical canal, comprising:
    a pliable ring having a lower edge and an upper edge and an outer surface between said lower and upper edges and an interior surface between said lower and upper edges;
    a pliable hollow, open-ended sleeve having a lower edge and an upper edge and an outer surface between said lower and upper edges of said sleeve and an interior surface between said lower and upper edges of said sleeve, said outer surface of the sleeve proximate the lower edge of the sleeve tapers radially inwardly so that the portion of said sleeve proximate the lower edge of the sleeve being more pliable than the portion of the sleeve proximate the upper edge of the sleeve permitting the transfer of an elastic load to stabilize and occlude the cervical canal;
    said sleeve generally supported within said ring and having a length between the lower and upper edges of the sleeve of between about 150% and about 200% of the length of said ring;
    said sleeve further including a plurality of apertures providing communication between the outer and interior surfaces;
    a biological beneficial medication coating the interior surface of said sleeve;
    a pliable annular member having an outer edge and an inner edge, said outer edge of said annular member attached to the upper edge of said ring and the inner edge of said annular member attached to the upper edge of the sleeve supporting said sleeve within said ring, said annular member having a superior surface between the outer edge and inner edge of said annular member and an inferior surface opposite said superior surface, said superior surface being generally perpendicular with said outer surface of said ring; and
    said pliable ring, pliable sleeve, and pliable annular member comprising medical-grade silicone,
    wherein said pliable ring, sleeve, and annular member permit the pessary to be placed into a rolled circular configuration for insertion into the vagina so that upon final placement of the pessary within the vagina at least a portion of the interior surface of said sleeve contacts at least a portion of the cervix and at least a portion of the superior surface of said annular member and at least a portion of the outer surface of the ring contact at least a portion of the vagina.

2. The pessary according to claim 1 wherein said pessary includes a plurality of radially oriented apertures along the upper edge of ring.

3. The pessary according to claim 1 wherein said pessary includes a plurality of radially oriented apertures along the outer edge of the annular member.

4. The pessary according to claim 1 wherein the length of said sleeve is at least twice the length of said ring.

5. The pessary according to claim 1 wherein the medication comprises progesterone.

6. The pessary according to claim 1 wherein the medication comprises prostaglandin inhibitors.

7. The pessary according to claim 1 wherein the superior surface of the annular member is coated with the biological beneficial medication.

8. The pessary according to claim 7 wherein the medication comprises progesterone.

9. The pessary according to claim 7 wherein the medication comprises prostaglandin inhibitors.

10. The pessary according to claim 1 wherein the outer surface of said ring is coated with the biological beneficial medication.

11. The pessary according to claim 10 wherein the medication comprises progesterone.

12. The pessary according to claim 10 wherein the medication comprises prostaglandin inhibitors.

13. The pessary according to claim 1, said pessary further comprising a sensor supported within the sleeve.

14. The pessary according to claim 13 wherein said sensor generates a signal indicative of the pH of the patient proximate the cervix.

15. The pessary according to claim 13 wherein said sensor generates a signal indicative of the temperature of the patient proximate the cervix.

16. The pessary according to claim 13 wherein said sensor generates a signal indicative of the movement of the patient's cervix.

17. The pessary according to claim 13 wherein said sensor generates a signal indicative of the orientation of the patient.

18. The pessary according to claim 13 wherein said sensor generates a signal indicative of the presence of contractions of the uterus.

19. The pessary according to claim 13 wherein said sensor generates a signal indicative of premature uterine contractions.

20. The pessary according to claim 13 wherein said sensor is configured to receive a signal and generate an electrical current to within the uterus.

21. The pessary according to claim 20 wherein the electrical current serves to interrupt premature contractions of the uterus.

22. The pessary according to claim 1 wherein said ring, sleeve, and annular member have a hardness of between about Shore20A and about Shore60A.

23. The pessary according to claim 22 wherein said ring, sleeve, and annular member have a hardness of between about Shore30A and about Shore50A.

24. A pessary device to prevent the preterm birth of a fetus through the cervical canal, comprising:
a pliable ring having a lower edge and an upper edge and an outer surface between said lower and upper edges and an interior surface between said lower and upper edges, wherein said ring includes a plurality of radially oriented apertures along the upper edge of said ring;
a pliable hollow, open-ended sleeve having a lower edge and an upper edge and an outer surface between said lower and upper edges of said sleeve and an interior surface between said lower and upper edges of said sleeve, said outer surface of the sleeve proximate the lower edge of the sleeve tapers radially inwardly so that the portion of said sleeve proximate the lower edge of the sleeve being more pliable than the portion of the sleeve proximate the upper edge of the sleeve permitting the transfer of an elastic load to stabilize and occlude the cervical canal;
said sleeve generally supported within said ring and having a length between the lower and upper edges of the sleeve of between about 150% and about 200% of the length of said ring;
said sleeve further including a plurality of apertures providing communication between the outer and interior surfaces;
a biological beneficial medication coating the interior surface of said sleeve;
a pliable annular member having an outer edge and an inner edge, said outer edge of said annular member attached to the upper edge of said ring and the inner edge of said annular member attached to the upper edge of the sleeve supporting said sleeve within said ring, said annular member having a superior surface between the outer edge and inner edge of said annular member and an inferior surface opposite said superior surface, said superior surface being generally perpendicular with said outer surface of said ring;
a sensor supported within the sleeve; and
said pliable ring, pliable sleeve, and pliable annular member comprising medical-grade silicone,
wherein said pliable ring, sleeve, and annular member have a hardness of between about Shore20A and about Shore60A permitting the pessary to be placed into a circular configuration for insertion into the vagina so that upon final placement of the pessary within the vagina at least a portion of the interior surface of said sleeve contacts at least a portion of the cervix and at least a portion of the superior surface of said annular member and at least a portion of the outer surface of the ring contact at least a portion of the vagina.

25. The pessary according to claim 24 wherein the medication comprises progesterone.

26. The pessary according to claim 24 wherein the medication comprises prostaglandin inhibitors.

27. The pessary according to claim 24 wherein the superior surface of the annular member is coated with the biological beneficial medication.

28. The pessary according to claim 27 wherein the medication comprises progesterone.

29. The pessary according to claim 27 wherein the medication comprises prostaglandin inhibitors.

30. The pessary according to claim 24 wherein the outer surface of said ring is coated with the biological beneficial medication.

31. The pessary according to claim 30 wherein the medication comprises progesterone.

32. The pessary according to claim 30 wherein the medication comprises prostaglandin inhibitors.

33. The pessary according to claim 24 wherein said sensor generates a signal indicative of the pH of the patient proximate the cervix.

34. The pessary according to claim 24 wherein said sensor generates a signal indicative of the temperature of the patient proximate the cervix.

35. The pessary according to claim 24 wherein said sensor generates a signal indicative of the movement of the patient's cervix.

36. The pessary according to claim 24 wherein said sensor generates a signal indicative of the orientation of the patient.

37. The pessary according to claim 24 wherein said sensor generates a signal indicative of the presence of contractions of the uterus.

38. The pessary according to claim 24 wherein said sensor generates a signal indicative of premature uterine contractions.

39. The pessary according to claim 24 wherein said sensor is configured to receive a signal and generate an electrical current to within the uterus.

40. The pessary according to claim 39 wherein the electrical current serves to interrupt premature contractions of the uterus.

* * * * *